United States Patent [19]

Ward

[11] Patent Number: 4,596,595

[45] Date of Patent: Jun. 24, 1986

[54] HERBICIDAL 5-AMINO-3-OXO-4-(SUBSTITUTED-PHENYL)-2,3-DIHYDROTHIOPHENE AND DERIVATIVES THEREOF

[75] Inventor: Carl E. Ward, San Jose, Calif.

[73] Assignee: Chevron Research Company, San Francisco, Calif.

[21] Appl. No.: 623,805

[22] Filed: Jun. 22, 1984

[51] Int. Cl.$^4$ .................. A01N 43/02; A01N 43/40; A01N 43/36; C07D 333/16

[52] U.S. Cl. ............................... 71/90; 71/91; 71/94; 71/95; 260/239 A; 260/239 BE; 260/239 B; 546/212; 546/280; 548/527; 549/63

[58] Field of Search .............. 549/63; 71/90, 91, 94, 71/95; 260/239 A, 239 BE, 239 B; 546/212, 280; 548/527

[56] References Cited

U.S. PATENT DOCUMENTS 4,441,910  4/1984  Shapiro ........................ 71/90

FOREIGN PATENT DOCUMENTS

| 42-19090 | 9/1967 | Japan . |
| 44-13710 | 6/1969 | Japan . |
| 1521092 | 8/1978 | United Kingdom . |
| 2080289 | 2/1982 | United Kingdom . |
| 767105 | 9/1980 | U.S.S.R. . |

OTHER PUBLICATIONS

Capraro et al, Helvetica Chmica Acta–vol. 66, Fasc. 1 (1983)–Nr. 31, pp. 362–378.
Umio, et al, Chem. Abstracts, vol. 70, 1969, 68123t.
Volovenko et al; Chem. Abstracts, vol. 95, 1981, 24799e.

Primary Examiner—Alan Siegel
Attorney, Agent, or Firm—T. G. DeJonghe; L. S. Squires

[57] ABSTRACT

5-Amino-3-oxo-4-(3-substituted-phenyl)-2,3-dihydrothiophene and derivatives thereof. The compounds exhibit herbicidal activity. At low dosages the compounds exhibit plant-growth regulating activity.

39 Claims, No Drawings

HERBICIDAL 5-AMINO-3-OXO-4-(SUBSTITUTED-PHENYL)-2,3-DIHYDROTHIOPHENE AND DERIVATIVES THEREOF

BACKGROUND OF THE INVENTION

This invention relates to 5-amino-3-oxo-4-(substituted phenyl)-2,3-dihydrothiophene derivatives and to the use of such compounds as herbicides and plant growth regulators.

Japanese Pat. No. 19090 (Chemical Abstracts 69P10352e) generically discloses certain 5-amino-3-oxo-4-(phenyl or halophenyl)-2,3-dihydrothiophenes, including 5-amino-3-oxo-4-(phenyl and 4-chlorophenyl)-2,3-dihydrothiophenes, as pharmaceuticals. Based on Chem. Abstracts 95: 24799e, Russian Pat. No. SU 767105, discloses 5-amino-3-oxo-4-(4-methoxyphenyl)-2,3-dihydrothiophene.

Chemiker-*Zeitung* 104 (1980) No. 10, Pages 302-303, is an academic paper disclosing the ring closure of 1-(dimethylamino)-2,4-diphenyl-1-buten-3,4-dione to yield 5-dimethylamino-2,4-diphenyl-2,3-dihydrofuran. British Pat. No. 1,521,092, discloses certain 3-phenyl-5-substituted-4(1H)-pyrid-ones or -thiones as herbicides. Japanese Patent Application 13,710/69 (Chemical Abstracts 71:61195e) discloses 5-amino-3-oxo-4-(phenyl or 4-chlorophenyl)-2,3-dihydrofurans and Japanese Pat. No. 68/21423 discloses p-(2-amino-4,5-dihydro-4-oxo-3-thienyl)-benzene sulfonic acid. *Helvetica Chemica Acta*, Volume 66, Pages 362-378 (1983) discloses 5-N-cyclopropyl-4-phenyl-2-methoxycarbonylmethylene-3-furanone as part of an academic chemical synthesis discussion. U.S. Pat. No. 4,441,910 discloses herbicidal ureidosulfonylfurans and ureidosulfonylthiophenes.

In my co-pending application Ser. No. 505,169, filed June 17, 1983, and Ser. No. 607,610 filed May 9, 1984, I disclose certain herbicidal 5-amino-3-oxo-4-(substituted phenyl)-2,3-dihydrofurans and derivatives thereof.

SUMMARY OF THE INVENTION

The present invention provides compounds having both pre-emergence and post-emergence herbicidal activity and having especially good pre-emergence activity against a broad spectrum of both broad-leaf weeds and grassy weeds. At lower application rates the compounds can be applied as plant growth regulators.

The compounds of the present invention can be represented by the following formula:

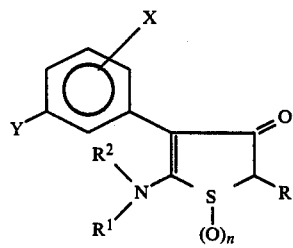

(I)

wherein n is 0, 1, or 2; R is lower alkyl having 1 through 4 carbon atoms; cycloalkyl having 3 through 7 carbon atoms, (cycloalkyl)alkylene having 3 through 7 carbon atoms in the cycloalkyl moiety and 1 through 3 carbons in the alkylene moiety; lower alkenyl; haloalkyl having 1 through 4 carbon atoms and 1 through 3 halo atoms independently selected from the group of fluoro, chloro, bromo or iodo; haloalkenyl having 2 through 4 carbon atoms and 1 through 3 halo atoms independently selected from the group of fluoro, chloro, bromo, or iodo; lower alkoxy; lower alkylthio; lower alkoxyalkyl wherein the alkoxy and alkyl moiety thereof independently have 1 through 3 carbon atoms; lower alklylthioalkyl wherein the alkyl moieties independently have 1 through 3 carbon atoms; phenyl, naphth-1-yl, inden-1-yl; 4-fluorophenyl; arylalkylene having 1 through 3 carbon atoms in the alklyene moiety and wherein said aryl moiety is phenyl, naphth-1-yl or inden-1-yl; or substituted aryl or arylalkylene selected from the group having the formulas:

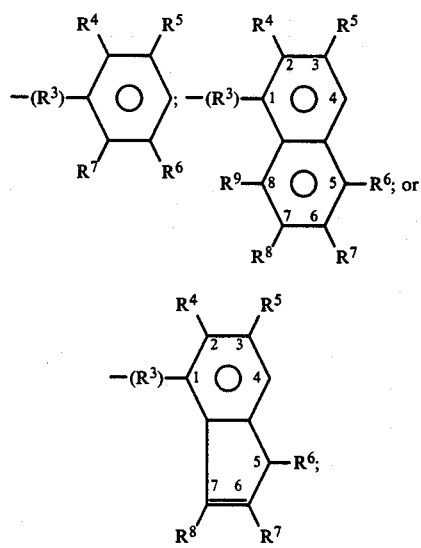

wherein one, two or three of $R^4$, $R^5$, $R^6$, $R^7$, $R^8$, and $R^9$ are independently selected from the group of lower alkyl, lower alkoxy, halo, nitro, or haloalkyl having 1 through 3 carbon atoms and 1 through 3 of the same or different halo atoms, and the remainder of $R^4$, $R^5$, $R^6$, $R^7$, $R^8$ and $R^9$ are hydrogen; and $R^3$ is a single bond or an alkylene having 1 through 3 carbon atoms; $R^1$ is hydrogen or alkyl having 1 through 4 carbon atoms; $R^2$ is hydrogen, alkyl having 1 through 4 carbon atoms, alkenyl having 3 or 4 carbon atoms, alkoxycarbonylalkyl having from 1 through 4 carbon atoms in the alkoxy moiety and from 1 through 4 carbon atoms in the alkyl moiety; alkoxyalkyl wherein the alkoxy and alkyl moieties independently have 1 through 3 carbon atoms, or alkylthioalkyl wherein the alkyl moieties independently have 1 through 3 carbon atoms; or $R^1$ and $R^2$ together with the nitrogen to which they are joined form a saturated or unsaturated nitrogen heterocycle having from 3 through 6 ring atoms one of which is nitrogen and the remainder of which are carbon atoms;

X is hydrogen, lower alkyl, lower alkoxy, halo, or trifluoromethyl and can be at any available position on the phenyl ring; and Y is lower alkyl; lower alkoxy; halo; lower haloalkyl having 1 through 4 carbon atoms, and 1 through 3 of the same or different halo atoms; lower haloalkoxy having 1 through 4 carbon atoms and 1 through 3 of the same or different halo atoms; or lower haloalkylthio having 1 through 4 carbon atoms and 1 through 3 of the same or different halo atoms; with the proviso that when Y is halo then R, R¹ and R² are not all hydrogen and the further proviso that when Y is other than trifluoromethyl and X is other than hydrogen, and R¹ is hydrogen and R² is hydrogen then R is methyl, ethyl, propyl, 2-halophenyl, 2-lower alkylphenyl or 4-fluorophenyl.

The invention also comprises compatible salts of the compound of Formula (I), for example salts obtained via replacement of the amino hydrogen (i.e., R¹ and R² is hydrogen) with a compatible cation or enolation of the 3-oxo group following replacement of the amino hydrogen.

The compounds of Formula I can exist as oxo-enol tautomers. The compounds of Formula (I) also have an asymmetric carbon atom and when n=1 have an asymmetric sulfur and can exist as optical isomers and/or diastereomers. The above formula is intended to encompass the respective tautomers and optical and geometric isomers where they exist as well as mixtures thereof and the respective isomers as well as mixtures thereof are encompassed within the invention.

It has also been discovered that generally the presence of a 3-trifluoromethyl substituent on the 4-phenyl group of the compounds of the present invention very substantially enhances herbicidal activity.

In a further aspect the invention provides a herbicidal composition comprising a compatible carrier and a herbicidally effective amount of the compounds of Formula (I), or compatible salts thereof, or mixtures thereof.

The present invention also provides a method for preventing or controlling the growth of unwanted vegetation, which comprises treating the growth medium and/or the foliage of such vegetation with a herbicidally effective amount of the compound(s) of Formula (I) and/or compatible salts thereof.

In another aspect, the present invention provides a plant growth regulating composition comprising a compatible carrier and a plant growth regulating amount of the compound of Formula (I), compatible salts of Formula (I), or mixtures thereof, effective to alter the normal growth pattern of said plants.

The present invention also provides a method for regulating plant growth which comprises treating the growth medium and/or the foliage of such vegetation with a plant growth regulating effective amount of the compound(s) of Formula (I) and/or compatible salts thereof, effective to alter the normal growth pattern of said plants.

The present invention also provides chemical intermediates and processes for preparing the compounds of Formula (I).

The invention will be further described hereinbelow.

FURTHER DESCRIPTION OF THE INVENTION AND THE PREFERRED EMBODIMENTS

Illustrations of typical compounds of Formula (I) of the present invention can be had by refernce to Examples 1, 3-8 set forth hereinbelow. In terms of substituents, the preferred compounds are those wherein R is hydrogen, methyl, ethyl, propyl, phenyl or monosubstituted phenyl, more preferably, methyl, ethyl, n-propyl, phenyl or monohalo or monomethyl-substituted phenyl, and especially ethyl, n-propyl; phenyl, 2-chlorophenyl, 2-methylphenyl and 2-fluorophenyl, n is preferably 0, R¹ and R² are preferably independently hydrogen, methyl, ethyl or n-propyl, and more preferably one of R¹ or R² is hydrogen and the other is methyl, ethyl or n-propyl, preferably methyl or ethyl; Y is preferably lower haloalkyl and especially trifluoromethyl. X is generally preferably hydrogen. The preferred compounds have at least one preferred substituent (preferably the Y substituent) and more preferably have a combination of preferred substituents.

SYNTHESIS

The compounds of Formula (I) wherein R¹ and R² are each hydrogen can be prepared by the following schematically represented process:

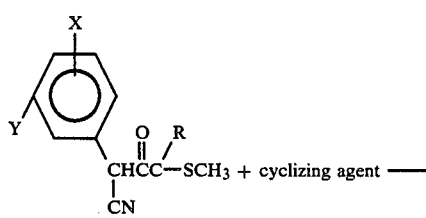

(A)

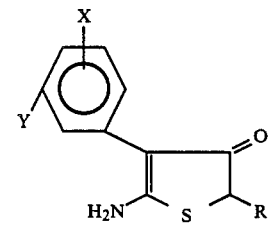

(Ia)

wherein X, Y, and R are as defined hereinabove.

This process can be conveniently effected by contacting Compound (A) with a cyclizing agent, under reactive conditions, preferably in the presence of an inert organic solvent.

Typically, this process is conducted at temperatures in the range of about from 0° to 200° C., preferably about from 115° to 120° C., for about from 10 to 120 minutes, preferably about from 10 to 30 minutes, using about from 1 to 10, preferably 1 to 2 moles of cyclizing agent per mole of Compound (A). Suitable cyclizing agents which can be used include, for example, strong anhydrous acid, for example, sulfuric acid, hydrogen chloride, hydrogen bromide, trifluoroacetic acid, methane sulfonic acid, and the like. Suitable organic solvents which can be used include, for example, acetic acid, propionic acid, butyric acid, toluene, xylene, and the like, and compatible mixtures thereof.

Best results are obtained using anhydrous sulfuric acid as the cyclizing agent.

The starting materials of Formula A wherein R is hydrogen, lower alkyl, cycloalkyl, alkoxy, alkoxyalkyl, alkylthioalkyl, lower haloalkyl, lower haloalkenyl, arylalkylene, substituted arylalkylene or alkenylalkyl (e.g., —CH₂CH═CH) can be prepared by the following schematically represented overall reaction equation:

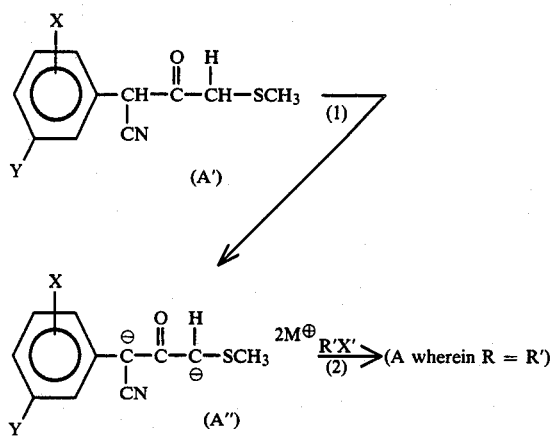

(A')

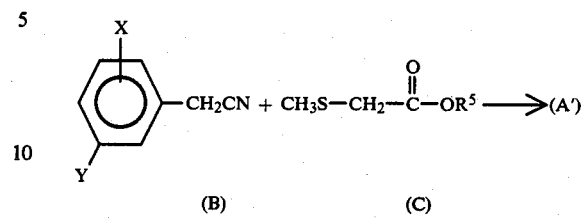

wherein X' is chloro, bromo, or iodo (preferably iodo); M is sodium or lithium, R' is hydrogen, lower alkyl, cycloalkyl, alkoxy, alkoxyalkyl, alkylthioalkyl, lower haloalkyl, lower haloalkenyl arylalkylene, substituted arylalkylene or alkenylalkyl; and X and Y are as defined hereinabove.

This process is conveniently conducted in two steps by first contacting compound (A') with an alkali metal amide (preferably $[(CH_3)_3Si]_2N^{\ominus}Li^{\oplus}$) under reactive conditions to form an immediate dianion salt. Step 1 is preferably conducted in an inert organic solvent. In the second step, preferably conducted in situ, the reaction product of the first step (i.e., A'') is contacted with the appropriate R'X', under reactive conditions to yield the desired R substitution. This reaction is also preferably conducted in an inert organic solvent. Also, both steps of this process are preferably conducted under anhydrous conditions under an inert atmosphere such as, for example, nitrogen.

Typically, step 1 of this process is conducted at temperatures in the range of about from $-100°$ to $25°$ C., preferably about from $-78°$ to $25°$ C., for about from ½ to 5 hours, preferably ½ to 1½ hours, using about from 1 to 5 moles, preferably 2 to 2.5 moles, of alkali metal amide salt per mole of compound A. Suitable alkali metal amides which can be used include, for example, lithium bis(trimethylsilyl)amide (i.e. $[(CH_3)_3Si]_2N^{\ominus}Li^{\oplus}$); sodium bis(trimethylsilyl)amide; potassium (trimethylsilyl)amide; lithium diethylamide; lithium diisopropylamide; sodium dimethylamide, and the like. The alkali metal amides are generally known compounds and can be prepared by known procedures, or obvious modifications thereof, for example, by the reaction of a secondary amine with n-butyl alkali metal. Lithium bis(trimethylsilyl)amide is preferred as it gives very good results and can be conveniently obtained from commercial sources. Suitable inert solvents, which can be used, include, for example, tetrahydrofuran, dioxane, dimethoxyethane, diethyl ether, diisopropyl ether, and the like and compatible mixtures thereof.

The second step of this process is typically conducted at temperatures in the range of about from $-30$ to $30°$ C., preferably, $22°$ to $25°$ C. for about from 1 to 18 hours preferably 1 to 5 hours using about from 1 to 10 moles, preferably 1 to 1.5 moles of RX' per mole of A'. The R'X' halides are generally known compounds and can be prepared by known procedures or obvious modifications thereof (e.g., substitution of appropriate reactants and solvents).

The starting materials of Formula (A') can be prepared by the following schematically represented process:

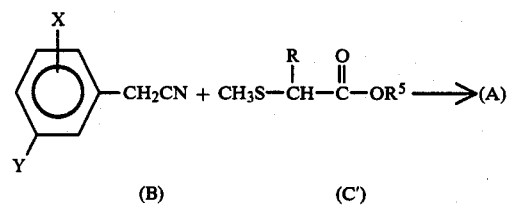

wherein $R^5$ is lower alkyl (e.g., methyl or ethyl), aryl (e.g. phenyl) or arylalkylene (e.g. benzyl); and, Y and X are as defined hereinabove.

This process can be conveniently effected by contacting Compound (B) with Compound (C), and a strong base under reactive conditions, preferably in an inert organic solvent.

Typically, this process is conducted at temperatures in the range of about from 0° to 100° C., preferably 75° to 85° C., for about from 5 to 36 hours, preferably 18 to 24 hours, using about from 1.0 to 10.0, preferably 1.0 to 1.2 moles of Compound (C) per mole of Compound (B). Typically, about from 1.0 to 10.0 moles of base are used per mole of Compound (C).

Suitable strong bases which can be used include, for example, alkali metal alkanolates, for example, sodium methoxide, sodium ethoxide, potassium ethoxide, sodium hydride, potassium hydride, and the like. The strong base should preferably be one which does not yield water as a by-product in this reaction system.

Suitable inert solvents which can be used include, for example, lower alkanols (for example, methanol, ethanol, and propanol) tetrahydrofuran, dimethoxyethane, dioxane, and the like, and compatible mixtures thereof. Conveniently, the alkali metal alkanolate is prepared in situ by reacting an alkali metal with excess alkanol which in turn serves as solvent for the above reaction.

The starting materials of Formulas (B) and (C) are generally known materials and can be prepared by known procedures, or obvious modifications thereof (i.e., substitution of appropriate starting materials). The preparation of Compound (B) is for example described in Org. Syn. Coll., Volume 1, 107 (1941), and the preparation of Compound (C) is described in Methoden Der Organischen Chemie (Houben-Weyl) vol. IX page 107 (1955).

A general procedure for preparing the starting materials of Formula A can be made by the following schematically represented by the overall reaction equation:

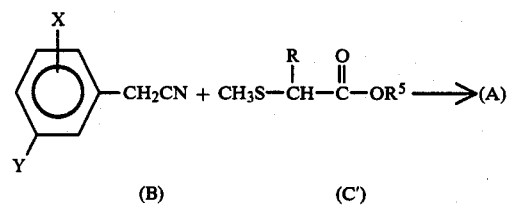

wherein R, X, and Y are as defined hereinabove and $R^5$ is lower alkyl, preferably methyl.

This process can be conveniently effected by contacting Compound (B) with Compound (C'), and a strong base, under reactive conditions, preferably in an inert organic solvent.

Typically, this process is conducted at temperatures in the range of about from 0° to 100° C., preferably 75° to 85° C. for about from 5 to 36 hours, preferably 18 to 24 hours, using about from 1.0 to 10.0, preferably 1.0 to 1.2 moles of Compound (C') per mole of Compound (B). This process can also be conveniently conducted at room temperature. Typically, about from 1.0 to 10.0 moles of base are used per mole of Compound (C').

Suitable strong bases which can be used include, for example, alkali metal alkanolates, for example, sodium methoxide, sodium ethoxide, potassium ethoxide, sodium hydride, potassium hydride, and the like. The strong base should preferably be one which does not yield water as a by-product in this reaction system.

Suitable inert solvents which can be used include, for example, lower alkanols (for example, methanol, ethanol, and propanol) tetrahydrofuran, dimethoxyethane, dioxane, and the like, and compatible mixtures thereof. Conveniently, the alkali metal alkanolate is prepared in situ by reacting an alkali metal with excess alkanol which in turn serves as solvent for the above reaction.

As pointed out above, the starting materials of Formula B are known compounds or can be prepared by obvious modifications of known procedures. The starting materials of formula C' can be prepared by the following schematically represented overall reaction equation:

$$Z-\underset{R}{\underset{|}{C}}H\underset{O}{\overset{\parallel}{C}}OR^5 + CH_3SH \longrightarrow (C')$$

(D)   (E)

wherein Z is chloro or bromo and R and $R^5$ are as defined hereinabove.

This process can be conveniently effected by contacting Compound (D) with methyl mercaptan (E) under reactive conditions preferably in an inert organic solvent and in the presence of a scavenger base to react with the hydrogen halide by-product of the reaction.

Typically, this process is conducted at temperatures in the range of about from 0°–40° C., preferably 0°–25° C., using about from 0.8 to 2 moles, preferably 1.1 to 1.5 moles of methyl mercaptan per mole of Compound (D). Suitable solvents which can be used include for example methylene chloride, tetrahydrofuran, 1,2-dichloroethane, chloroform, carbon tetrachloride and the like and compatible mixtures thereof. Suitable scavenger bases which can be used include, for example, triethylamine; pyridine; methylpyridine; 1,5-diazabicyclo [4.3.0] nonene; 1,8-diazabicyclo [5.4.0]undec-7-ene; sodium bicarbonate, potassium bicarbonate, sodium hydroxide, potassium hydroxide, alkali metal alkoxides (e.g., sodium methoxide, potassium ethoxide) and the like. Typically about 0.9 to 1.5 mole equivalents of scavenger base are used per mole of Compound (D).

The starting materials of Formula (D) can be prepared by applying the procedure described in Org. Syn. Coll. Vol. III, 381 (1955) using the appropriate starting materials. The starting materials of Formula (D) wherein R=phenyl or substituted phenyl can also be prepared via the following schematically represented overall reaction equation:

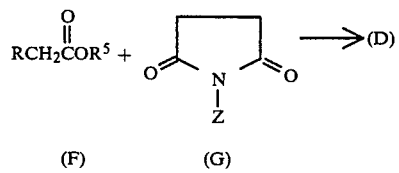

(F)   (G)

wherein R, $R^5$ and Z are as defined hereinabove.

This process can be conveniently conducted by contacting Compound F with N-bromo or chloro-succinimide (G) under reactive conditions preferably in an inert organic solvent.

Typically, this process is conducted at temperatures in the range of about from 40° to 100° C., preferably 60° to 80° C., using from 0.9 to 1.5 moles of the N-halosuccinimide (G) per mole of Compound (F). Suitable solvents which can be used include, for example, carbon tetrachloride; 1,2-dichloroethane, methylene chloride, chlorobenzene, chloroform, and the like and compatible mixtures thereof.

The starting materials of Formula F are generally known materials and can be prepared by known procedures, or obvious modifications thereof (i.e., substitution of appropriate starting materials). A preparation for Compound (F) is described in Org. Syn. Coll., Volume 1, 270 (1941). N-bromo and N-chlorosuccinimide are, of course, well known commercial compounds.

The compounds of Formula (I) wherein $R^1$ and $R^2$ are each hydrogen and R is aryl or substituted aryl are preferably prepared via the following schematically represented process:

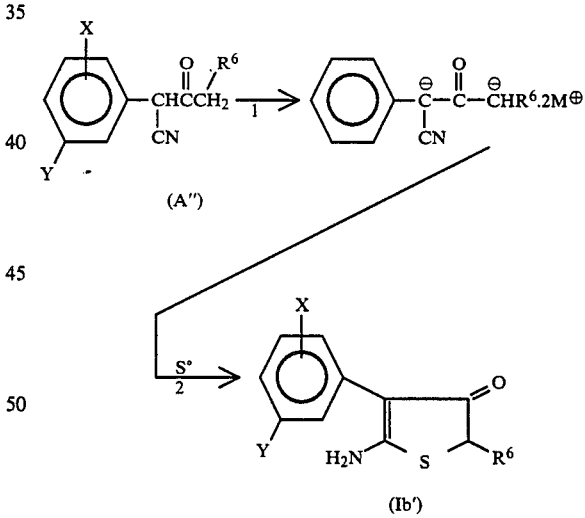

wherein $R^6$ is aryl or substituted aryl, M is an alkali metal anion, and X and Y are as defined hereinabove.

This process is conveniently conducted in two steps by first contacting compound A″ with an alkali metal amide under reactive conditions, preferably in an inert organic solvent or organic carrier liquid. The reaction product of the first step can then be contacted with elemental sulfur, conveniently in situ, under reactive conditions.

The first step is typically conducted at temperatures in the range of about from −78° to 25° C., preferably −30° to 22° C., for about from ½ to 5 hours, preferably about from ½ to 2 hours, using about from 2 to 10 moles, preferably 2 to 2.5 moles, of alkali metal amide per mole of compound A. Suitable alkali amides and organic solvents or carrier liquids which can be used include those described with respect to alkali metal reaction previously described hereinabove.

The second step of this process can then be effected by contacting the reaction product of the first step with elemental sulfur, preferably in an organic solvent or organic carrier liquid and most conveniently is conducted in situ. This step is typically conducted at temperatures in the range of about from 20° to 30° C., preferably 22° to 25° C., for about from 1 to 24 hours, preferably 18 to 24 hours, using about from 1 to 5, preferably 1 to 1.1 moles of elemental sulfur per mole of compound A″. Suitable inert organic solvents or organic carrier liquids include those described with respect to the first step of this process.

The starting materials of formula A″ can be prepared via the following schematically represented overall reaction equation:

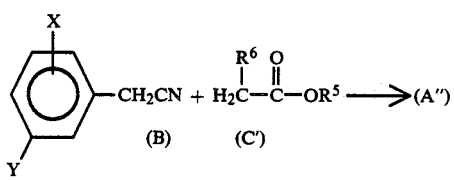

wherein $R^5$ and $R^6$ are as defined hereinabove.

This process can be effected in the same manner as described hereinabove with respect to the reaction of compounds B and C but replacing compound C with compound C′. This process can also be used to prepare the correponding analogs of A′ wherein $R^6$ is lower alkoxy or haloalkoxy by using the corresponding $R^6$ alkoxy or haloalkoxy analog of C′.

The compound of Formula (I) wherein one or both of $R^1$ and $R^2$ are lower alkyl or lower alkenyl and n=0 can be prepared by alkylation (or alkenylation) of the amino group:

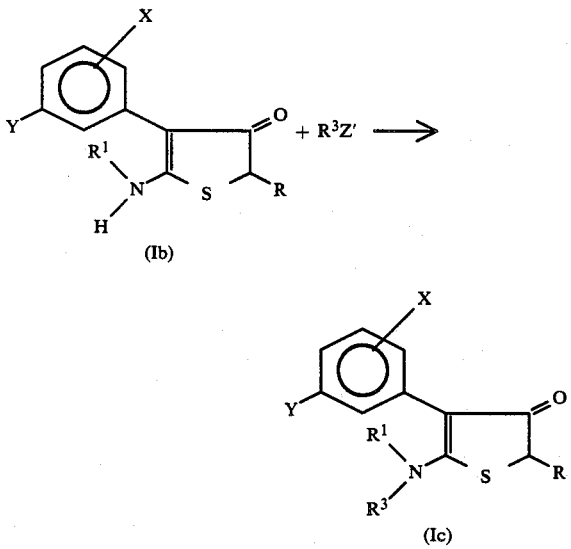

wherein
R, $R^1$, and X are as defined hereinabove;

$R^3$ is as defined for $R^2$ but is not hydrogen; and $R^3Z'$ is an alkylation agent having the desired $R^3$ group or $R^1$ if dialkylation is desired.

This process can be effected by contacting Compound (Ib) under reactive conditions with a suitable alkylation agent capable of alkylating primary or secondary amino groups.

For example, this can be effected by contacting Compound (Ib) with a $R^3$ halide, preferably $R^3I$ or $R^3Br$, preferably in an inert organic solvent and preferably in the presence of a scavenger base and a phase transfer agent. Typically, this process is conducted at temperatures in the range of about from 0° to 100° C., preferably 20° to 45° C. for about from 1.0 to 72.0, preferably 2.0 to 18.0 hours. Where it is desired to monoalkylate, typically about from 1.0 to 1.1 moles of $R^3Z'$ reactant is used per mole of Compound (Ib). Where it is desired to dialkylate, typically about from 1.9 to 4.0 moles of $R^3Z'$ are used per mole of Compound (Ib). In the case where it is desired to prepare the compound wherein $R^3$ is alkoxyalkyl or alkylthioalkyl, it is preferred to use a large excess of $R^3$ halide even where monoalkylation is desired; for example 3 to 6 moles of $R^3Z'$ per mole of Ib. Further alkylation can be effected in a second step if desired. Variation in $R^1$ and $R^2$ can be effected by first alkylation of only one of the two amino hydrogens and then alkylating the second amino hydrogen with an alkylating agent having a different $R^3$ alkyl or alkenyl group. The compounds wherein $R^1$ and $R^2$ together with the amino nitrogen atoms form a saturated heterocycle can be prepared by using the appropriate $Z''$—$(CH_2)_{2-5}$—$Z'$, wherein $Z''$ and $Z'$ are I or Br alkylating agent. Th $R^1R^2N$ unsaturated heterocycle can be prepared by using the appropriate cis-alkenyl dihalide, wherein one of the halo atoms is on each of the terminal alkenyl carbons.

Suitable inert organic solvents which can be used, include, for example, liquid halogenated alkanes; for example, methylene chloride, carbon tetrachloride, dichloroethane; tetrahydrofuran and the like. Suitable scavenger bases include, for example, alkali hydroxides or the bases described hereinabove with respect to the reaction of Compound (B) with Compound (C). Suitable phase transfer agents are agents which transfer hydrophilic ions into a lipophilic organic medium and include, for example, benzyl triethylammonium chloride, tetra-n-butylammonium chloride, methyltrioctylammonium chloride, and the like.

The compounds of Formula (Ic) wherein $R^3$ is lower alkyl (e.g. methyl) and $R^1$ is hydrogen or lower alkyl, are advantageously prepared using dialkyl sulfate as the alkylating agent. This can be conveniently effected by contacting the compound of Formula (Ib) with the desired lower alkyl sulfates in the presence of a strong base and preferably in an inert organic solvent in the presence of a phase transfer agent. Typically, this process is conducted at temperatures in the range of about from 0° to 100° C., preferably 20° to 45° C., using about from 1.0 to 4.0 moles of dialkyl sulfate per mole of Compound (I′). An excess, typically about 2.5 mole of base is used.

Preferably, this process is also conducted base is used in an inert organic solvent such as, for example, tetrahydrofuran, carbon tetrachloride, dichloroethane, and the like.

Suitable strong bases which can be used include, for example, sodium hydroxide, potassium hydroxide, sodium ethoxide, sodium carbonate, potassium carbonate, and the like. Suitable phase transfer agents are agents which transfer hydrophilic ions into a lipophilic organic medium and include, for example, benzyl triethylammonium chloride, tetra-n-butylammonium chloride, methyltrioctylammonium chloride, and the like.

My colleagues M. Haire, et al., have discovered that conducting the alkyl iodide and alkyl sulfate alkylation processes using an inert organic solvent in which the base is insoluble (for example, using potassium carbonate or sodium hydroxide in methylene chloride) in the absence of a phase transfer agent improves the selectivity of the process for monoalkylation. The speed of the reaction is increased by using a phase transfer agent (e.g., benzyl triethylammonium chloride) but selectivity is lost. The process is further improved by using a phase transfer agent which functions as both the phase transfer agent and the base, such as benzyltrimethyl ammonium hydroxide.

The alkylation etc., can also be felicitously effected via the procedure of my colleague P. Pomidor, by contacting ccmpound Ib with the desired aqueous $R^3$ primary amine, in methanol or ethanol at elevated temperatures (e.g., 90°–120° C., and pressures (e.g., 4–8 atmospheres).

The sulfoxide and sulfones of the invention can be conveniently prepared:

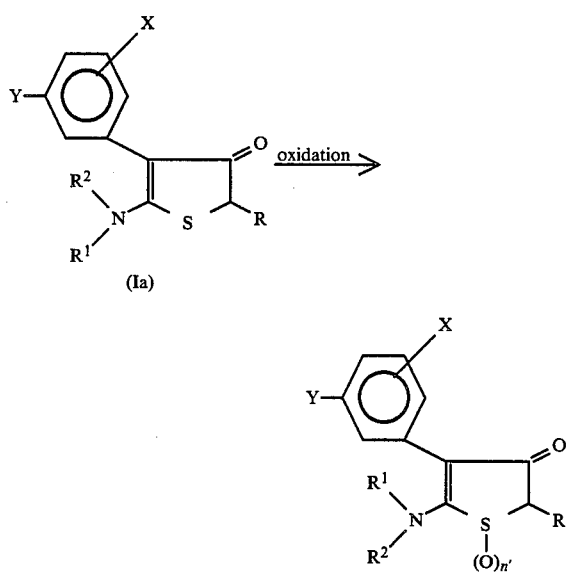

wherein R, $R^1$, $R^2$, X and Y are as defined herein and n' is 1 or 2.

Any suitable oxidation procedure can be used to effect the oxidation. Basically, the same procedure is used to prepare the sulfoxides and sulfones with the exception of the severity of the reaction conditions and/or the amount of the oxidizing agent.

In the case of the sulfoxides (n'=1) the oxidation can be effected by contacting the corresponding compound of formula Ia with about from 1.0 to 1.5 moles of oxidizing agent under reactive conditions preferably in an inert organic solvent. Typically, the oxidation is conducted at temperatures in the range of about from 0° to 45 ° C., preferably 20° to 25° C. for about from 1.0 to 48.0 hours, preferably 12.0 to 24.0 hours, using about from 1.0 to 2.0 moles, preferably 1.0 to 1.5 moles of oxidizing agent per mole of compound Ia.

In the case of the sulfones (n'=2) the reaction typically conducted at temperatures in the range of about from 0° to 45° C., preferably 20° to 25° C., for about from 24 to 72 hours, preferably 24 to 48 hours using about from 1.0 to 6.0 moles, preferably 2.0 to 4.0 moles of starting materials per mole of compound Ia.

Suitable oxidizing agents which can be used include, for example, m-chloroperbenzoic acid, hydrogen peroxide, sodium periodate, potassium permanganate, peracetic acid, and the like. Suitable solvents which can be used include, for example, methylene chloride, chloroform, carbon tetrachloride, acetic acid, water, and the like, and compatible mixtures thereof.

The compatible salts of Formula (I) can be prepared by conventional procedures by treating the compound of Formula (I) with a suitable strong base such as, for example, n-butyllithium, sodium hydride, potassium hydride, and the like, having the desired cation, by conventional procedures. The enolate salts can be prepared by treating the $R^1$ and/or $R^2$ cation salts with base in accordance with conventional procedures. Additional variations in the salt cation can also be effected via ion exchange with an ion exchange resin having the desired cation.

GENERAL PROCESS CONDITIONS

In the above-described processes, it is generally preferable to separate the respective products before proceeding with the next step in the reaction sequence, except where described as an in situ step or unless otherwise expressly stated. These products can be recovered from their respective reaction product mixtures by any suitable separation and purification procedure, such as, for example, recrystallization and chromatography. Suitable separation and purification procedures are, for example, illustrated in the Examples set forth hereinbelow.

Generally, the reactions described above are conducted as liquid phase reactions and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole ratios of reactants, solvents, etc.) have been given, that other process conditions could also be used. Optimum reaction conditions (e.g., temperature, reaction time, mol ratios, solvents, etc.) may vary with the particular reagents or organic solvents used but can be determined by routine optimization procedures.

Where optical isomer mixtures are obtained respective optical isomers can be obtained by conventional resolution procedures. Geometric isomers can be separated by conventional separation procedures which depend upon differences in physical properties between the geometric isomers.

DEFINITIONS

As used herein the following terms have the following meanings unless expressly stated to the contrary:

The term "lower alkyl" refers to both straight and branched-chain alkyl groups having a total of from 1 through 4 carbon atoms and includes primary, secondary and tertiary alkyl groups. Typical lower alkyls include, for example, methyl, ethyl, n-propyl, isopropyl, n-butyl, t-butyl.

The term "alkylene" refers to both straight chained and branched chained alkylene groups. The term "lower alkylene" refers to alkylenes having 1 through 4 carbon atoms and includes, for example, $$-CH_2-; \quad -CH_2-CH_2-; \quad -\underset{\underset{CH_3}{|}}{C}H_2CH_2-$$

and the like.

The term "lower alkenyl" refers to alkenyl groups having 2 through 6, preferably 2 through 4, carbon atoms and includes, for example, vinyl, 1-propenyl, 2-propenyl, 1-methylvinyl, 1-butenyl, 2-methylprop-1-enyl and the like.

The term "lower alkoxy" refers to the group $-OR'$ wherein R' is lower alkyl.

The term "lower alkylthio" refers to the group $-SR'$ wherein R' is lower alkyl.

The term "lower alkoxalkyl" refers to the group $R'OR''-$ wherein R' and R'' are independently straight chain or branched chain groups having 1 through 3 carbon atoms.

The term "lower alkylthioalkyl" refers to the group $R'SR''$ wherein R' and R'' are independently straight chain or chain alkyl groups having 1 through 3 carbon atoms.

The term "lower alkoxycarbonylalkyl" refers to the group $$R'O\underset{\underset{O}{\|}}{C}R''-$$

wherein R' is lower alkyl and R'' is alkylene having 1 through 4 carbon atoms and can be straight or branched chained. Typical alkoxycarbonylalkyl groups include for example, $-CH_2C(O)OCH_3$, $-CH(CH_3)COOC_2H_5$, and the like.

The term "halo" refers to the group of fluoro, chloro, bromo and iodo.

The term "lower haloalkyl" refers to haloalkyl compounds having 1 through 4 carbon atoms and 1 through 3 halo atoms independently selected from the group of fluoro, chloro, bromo and iodo. Preferably the lower haloalkyl group has 1 or 2 carbon atoms.

The term "lower haloalkoxy" refers to "lower alkoxy" groups having 1 through 3 halo atoms independently selected from the group of fluoro, chloro, bromo or iodo.

The term "aryl" refers to aryl groups having 6 through 10 carbon atoms and includes, for example, phenyl, naphthyl, indenyl. Typically the aryl group will be phenyl or naphthyl as compounds having such groups are more readily available commercially than other aryl compounds.

The term "substituted aryl" refers to aryl groups having 1 through 3 substituents independently selected from the group of lower alkyl, lower alkoxy, halonitro, or haloalkyl having 1 through 3 carbon atoms and 1 through 3 halo atoms. Typical substituted aryl groups include, for example, 2-fluorophenyl, 2-chlorophenyl, 2,6-dimethylphenyl, 4-fluorophenyl, 2-methylphenyl, 2-chloro,3-chloromethylphenyl, 2-nitro,5-methylphenyl, 2,6-dichlorophenyl, 3-trifluoromethylphenyl, 2-methoxyphenyl, 2-bromonaphth-1-yl, 3-methoxyinden-1-yl, and the like.

The term "arylalkylene" refers to the group $ArR^{3'}-$ wherein Ar is aryl and $R^{3'}$ is alkylene having 1 through 3 carbon atoms. $R^{3'}$ includes both straight-chained and branched-chained alkylenes, for example, methylene, ethyl, 1-methylethyl, and propyl.

The term "(substituted aryl)alkylene" or "ring-substituted arylalkylene" refers to the group $AR'R^{3'}-$ wherein Ar' is substituted aryl and $R^{3'}$ is alkylene as define with respect to arylalkylene.

The term "cycloalkyl" refers to cycloalkyl groups having 3 through 7 carbon atoms, for example cyclopropyl, cyclopentyl, cyclohexyl or the like.

The term "(cycloalkyl)alkylene" refers to the group $Y'R^{3'}$ wherein Y' is cycloalkyl and $R^{3'}$ is alkylene as defined hereinabove with respect to arylalkylene.

The term "saturated nitrogen heterocycle" as used herein with respect to $R^1$ and $R^2$ of formula I refers to the groups having the formula:

$$\underset{\underset{\underset{(CH_2)_n}{\diagdown\diagup}}{H_2C\diagdown \diagup CH_2}}{\overset{|}{N}}$$

wherein n is 1, 2, or 3.

The term "unsaturated nitrogen heterocycle" as used herein with respect to $R^1$ and $R^2$ of formula I refer to the groups having the formulas:

[structures of unsaturated nitrogen heterocycles] and

The term "compatible salts" refers to salts which not significantly adversely alter the herbicidal properties of the parent compound. Suitable salts include cation salts such as, for example, the cation salts of lithium, sodium, potassium, alkali earth metals, ammonia, quaternary ammonium salts, and the like.

The term "room temperature" or "ambient temperature" refers to about 20°–25° C.

UTILITY

The compounds of Formula (I) exhibit both pre-emergence and post-emergence herbicidal activity and exhibit especially good pre-emergence herbicidal activity. Also by varying the dosage rate certain of the compounds exhibit acceptable safety with respect to certain broadleaf crops, notably soybean crops, while retaining a broad spectrum of pre-emergence herbicidal activity against both broadleaf weeds and grasses.

Generally, for post-emergent applications, the herbicidal compounds are applied directly to the foliage or other plant parts. For pre-emergence applications, the herbicidal compounds are applied to the growth medium, or prospective growth medium, for the plant. The optimum amount of the herbicidal compound or composition will vary with the particular plant species, and the extent of plant growth, if any, and the particular part of the plant which is contacted and the extent of contact. The optimum dosage can also vary with the general location, or environment (e.g., sheltered areas such as greenhouses compared to exposed areas such as fields), and type and degree of control desired. Generally, for both pre- and post-emergent control, the present compounds are applied at rates of about from 0.02 to 60 kg/ha, preferably about from 0.02 to 10 kg/ha.

Also, although in theory the compounds can be applied undiluted, in actual practice they are generally applied as a composition or formulation comprising an effective amount of the compound(s) and an acceptable carrier. An acceptable or compatible carrier (agriculturally acceptable carrier) is one which does not significantly adversely affect the desired biological effect achieved by the active compounds, save to dilute it. Typically, the composition contains about from 0.05 to 95% by weight of the compound of Formula (I) or mixtures thereof. Concentrates can also be made having high concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for pre-emergence application agents which reduce the leachability of the compound or otherwise enhance soil stability.

The composition can also contain various compatible adjuvants, stabilizers, conditioners, insecticides, fungicides, and if desired, other herbicidally active compounds.

At reduced dosages the compounds of the present invention also exhibit plant growth regulating activity and can be used to alter the normal growth pattern of green plants.

The compounds of Formula (I) can be applied as plant growth regulators in pure form, but more pragmatically, as in the case of herbicidal application, are applied in combination with a carrier. The same types of carriers as set forth hereinabove with respect to the herbicidal compositions can also be used. Depending on the desired application, the plant growth regulating composition can also contain, or be applied in combination with other compatible ingredients such as desiccants, defoliants, surface-active agents, adjuvants, fungicides, and insecticides. Typically, the plant growth regulating composition will contain a total of about from 0.005 to 90 wt. % of the compound(s) of Formula (I) depending on whether the composition is intended to be applied directly or diluted first.

A further understanding of the invention can be had in the following non-limiting Preparation and Examples. Wherein, unless expressly stated to the contrary, all temperatures and temperature ranges refer to the Centigrade or Celcius system and the term "ambient" or "room temperature" refers to about 20°–25° C. The term "percent" or "%" refers to weight and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 60 mHz, signals are assigned as singlets (s), broad singlets (bs), doublets (d), double doublets (dd), triplets (t), double triplets (dt), quartets (q), and multiplets (m); and cps refers to cycles per second. Also where necessary preparations and examples are repeated to provide additional starting material for subsequent examples.

PREPARATIONS AND EXAMPLES

Preparation 1

(3-Trifluoromethylphenyl)-benzylcarbonyl-acetronitrile

In this example, 4.91 g of metallic sodium was added to 110 ml of anhydrous ethanol at room temperature and stirred until all of the sodium dissolved. A mixture containing 18.76 g of (3-trifluoromethylphenyl) acetonitrile and 21.73 g of ethyl phenylacetate was then added dropwise and the resulting mixture was stirred at reflux for about 18 hours. The mixture was then poured into 300 ml water and then extracted three times with ethyl ether. The pH of the extracted aqueous layer was then adjusted to a pH of about 1 with aqueous 10 wt. % hydrochloric acid and then again extracted three times with ethyl ether. The organic layer was then washed twice with saturated aqueous sodium bicarbonate, dried over magnesium sulfate and evaporated to dryness under vacuum affording 22.6 g of the title compound.

Similarly, by applying the above procedure using the appropriately substituted-phenyl acetonitrile and ethyl-substituted acetate starting materials, the following compounds can be prepared:

(5-chloro-3-trifluoromethylphenyl)-benzylcarbonyl-acetonitrile;
(4-chloro-3-trifluoromethylphenyl)-benzylcarbonyl-acetonitrile;
(2-bromo-3-trifluoromethylphenyl)-benzylcarbonyl-acetonitrile;
(6-fluoro-3-trifluoromethylphenyl)-benzylcarbonyl-acetonitrile;
(4-methyl-3-trifluoromethylphenyl)-benzylcarbonyl-acetonitrile;
(5-methoxy-3-trifluoromethylphenyl)-benzylcarbonyl-acetonitrile;
(6-iodo-3-trifluoromethylphenyl)-benzylcarbonyl-acetonitrile;
(3,5-di-trifluoromethylphenyl)-benzylcarbonyl-acetonitrile;
(3-trifluoromethylphenyl)-(2,6-difluorobenzylcarbonyl-acetonitrile;
(3-trifluoromethylphenyl)-(3-iodobenzyl)-acetonitrile;
(3-trifluoromethylphenyl)-naphth-1-ylmethylene-acetonitrile;

(3-trifluoromethylphenyl)-(2-methylnaphth-1-ylmethylene)-acetonitrile;
(3-trifluoromethylphenyl)-(3-ethoxynaphth-1-ylmethylene)-acetonitrile;
(3-n-butylphenyl)-benzylcarbonyl-acetonitrile;
(3-n-butoxyphenyl)-benzylcarbonyl-acetonitrile;
(3-trifluoromethylthiophenyl)-benzylcarbonyl-acetonitrile;
(3-difluoromethoxyphenyl)-benzylcarbonyl-acetonitrile;
(3-chloromethylthiophenyl)-benzylcarbonyl-acetonitrile;
(3-bromophenyl)-(2-nitrobenzylcarbonyl)-acetonitrile;
(2-chloro-3-propylphenyl)-(6-nitronaphth-1-ylmethylene)-acetonitrile;
(3-bromo-2-ethylphenyl)-naphth-1-ylmethylene-acetonitrile;
(3,6-difluorophenyl)-beta-naphth-1-ylethyl-acetonitrile;
(3-iodo-4-methylphenyl)-(2,7-difluoronaphth-1-ylmethylene)-acetonitrile;
(3-chlorophenyl)-benzylcarbonyl-acetonitrile;
[3-(2-fluoropropylthio)phenyl]-benzylcarbonyl-acetonitrile;
(3-t-butoxyphenyl)-benzylcarbonyl-acetonitrile;
[3-(2,3-dichloropropylthiophenyl)-benzylcarbonyl-acetonitrile;
(3-bromophenyl)-benzylcarbonyl-acetonitrile;
(3-iodophenyl)-(2,3-dinitrobenzylcarbonyl)-acetonitrile;
(3-fluorophenyl)-(8-trifluoromethylnaphth-1-ylmethylene)-acetonitrile;
(3-isopropoxyphenyl)-2-naphthylmethylene-acetonitrile;
(3-fluorophenyl)-(6-butyl-8-chloronaphth-1-ylmethylene-acetonitrile;
(3-trifluoromethylphenyl)-(3-nitronaphth-1-ylmethylene)-acetonitrile.
(3-iodophenyl)-(3-nitrobenzylcarbonyl)-acetonitrile;
(3-trifluoromethylphenyl)-(2,3-dichlorobenzylcarbonyl)-acetonitrile;
(3-methoxyphenyl)-1-naphthylmethylenecarbonyl-acetonitrile;
(3-trifluoromethyl)-(3-chloro-8-fluoronaphth-1-ylmethylenecarbonyl)-acetonitrile;
(3-trifluoromethyl)-[(2-trifluoromethyl-3-methyl-8methoxy-naphth-1-yl)methylenecarbonyl]-acetonitrile;
(3-trifluoromethyl)-(inden-1-ylmethylene-carbonyl)-acetonitrile; and
(3-trifluoromethyl)-(2-fluoroinden-1-yl-methylenecarbonyl)-acetonitrile.

Similarly, by applying the same procedure to the appropriate ethyl alkoxy substituted acetate the corresponding alkoxy acetonitrile analogs of the above compounds can be prepared, for example:
(3-trifluoromethylphenyl)-dimethoxyacetyl-acetonitrile;
(3-trifluoromethylphenyl)-(butoxymethoxyacetyl)-acetonitrile, etc.

The alkoxy compounds can be converted to the corresponding 2-alkoxy compounds of the invention via the procedure described in Example 3A hereinbelow.

EXAMPLE 1

2-Phenyl-3-oxo-4-(3-trifluoromethylphenyl)-5-amino-2,3-dihydrothiophene

In this example a solution containing 2.0 g of (3-trifluoromethylphenyl)-benzylcarbonyl-acetonitrile in 30 ml of tetrahydrofuran was added dropwise to 13.2 ml of a 1 molar mixture of lithium bis(trimethylsilyl)amide under anhydrous conditions at −70° C. The resulting mixture was stirred for ten minutes and then allowed to rise to room temperature and stirred for another 20 minutes. 0.21 g of powdered elemental sulfur was then admixed therewith and the resulting mixture stirred for about 18 hours. The mixture was then added to 200 ml of aqueous saturated ammonium chloride solution and then extracted three times with ethyl ether. The combined ether extracts were dried over magnesium sulfate and then concentrated by evaporation under vacuum affording 1.8 g of a crude solid of the title compound. The crude solid was chromatographed on silica gel eluting with 30% vol. ethyl acetate:70% petroleum ether to afford 0.4 g of the title compound.

Similarly, by applying the above procedure to the compounds listed in Preparation 1, the following compounds can be prepared:
2-phenyl-3-oxo-4-(5-chloro-3-trifluoromethylphenyl)-5-amino-2,3-dihydrothiophene;
2-phenyl-3-oxo-4-(4-chloro-3-trifluoromethylphenyl)-5-amino-2,3-dihydrothiophene;
2-phenyl-3-oxo-4-(2-bromo-3-trifluoromethylphenyl)-5-amino-2,3-dihydrothiophene;
2-phenyl-3-oxo-4-(6-fluoro--3-trifluoromethylphenyl)-5-amino-2,3-dihydrothiophene;
2-3-oxo-4-(4-methyl-3-trifluoromethylphenyl)-5-amino-2,3-dihydrothiophene;
2-phenyl-3-oxo-4-(5-methoxy-3-trifluoromethylphenyl)-5-amino-2,3-dihydrothiophene;
2-phenyl-3-oxo-4-(6-iodo-3-trifluoromethylphenyl)-5-amino-2,3-dihydrothiophene;
2-phenyl-3-oxo-4-(3,5-di-trifluoromethylphenyl)-5-amino-2,3-dihydrothiophene;
2-(2-nitrophenyl)-3-oxo-4-(3-trifluoromethylphenyl)-5-amino-2,3-dihydrothiophene;
2-(3-iodophenyl)-3-oxo-4-(3-trifluoromethylphenyl)-5-2,3-dihydrothiophene;
2-(naphth-1-yl)-3-oxo-4-(3-trifluoromethylphenyl)-5-amino-2,3-dihydrothiophene;
2-2-methylnaphth-1-yl)-3-oxo-4-(3-trifluoromethylphenyl)-5-amino-2,3-dihydrothiophene;
2-(3-ethoxynaphth-1-yl)-3-oxo-4-(3-trifluoromethylphenyl)-5-amino-2,3-dihydrothiophene; and
2-phenyl-3-oxo-4-(3-n-butylphenyl)-5-amino-2,3-dihydrothiophene;
2-phenyl-3-oxo-4-(3-n-butoxyphenyl)-5-amino-2,3-dihydrothiophene;
2-phenyl-3-oxo-4-(3-trifluoromethylthiophenyl)-5-amino-2,3-dihydrothiophene;
2-phenyl-3-oxo-4-(3-difluoromethoxyphenyl)-5-amino-3-dihydrothiophene;
2-phenyl-3-oxo-4-(3-chloromethylphenyl)-5-amino-2,3-dihydrothiophene;
2-(2-nitrophenyl)-3-oxo-4-(3-bromophenyl)-5-amino-2,3-dihydrothiophene;
2-(6-nitronaphth-1-yl)-3-oxo-4-(2-chloro-3propylphenyl)-5-amino-2,3-dihydrothiophene;
2-(naphth-1-yl)-3-oxo-4-(3-bromo-2-ethylphenyl)-5-amino-2,3-dihydrothiophene;
2-(naphth-1-yl)-3-oxo-4-(3,6-difluorophenyl)-5-amino-2,3-dihydrothiophene;
2-(2,7-difluoronaphth-1-yl)-3-oxo-4-(3-iodo-4-methylphenyl)-5-amino-2,3-dihydrothiophene;
2-phenyl-3-oxo-4-(3-chlorophenyl)-5-amino-2,3-dihydrothiophene;

2-phenyl-3-oxo-4-[3(2-fluoropropylthio)phenyl]-5-amino-2,3-dihydrothiophene;
2-phenyl-3-oxo-4-(3-t-butoxyphenyl)-5-amino-2,3-dihydrothiophene;
2-phenyl-3-oxo-4-[3(2,3-dichloropropylthiophenyl)]-5-amino-2,3-dihydrothiophene;
2-phenyl-3-oxo-4-(3-bromophenyl)-5-amino-2,3-dihydrothiophene;
2-(2,3-dinitrophenyl)-3-oxo-4-(3-iodophenyl)-5-amino-2,3-dihydrothiophene;
2-(8-trifluoromethylnaphth-1-yl)-3-oxo-4-(3-fluorophenyl)-5-amino-2,3-dihydrothiophene;
2-(naphth-1-yl)-3-oxo-4-(3-isopropoxyphenyl)-5-amino-2,3-dihydrothiophene;
2-(6-butyl-8-chloronaphth-1-yl)-3-oxo-4-(3-fluorophenyl)-5-amino-2,3-dihydrothiophene;
2(3-nitronaphth-1-yl)-3-oxo-4-(3-trifluoromethylphenyl)-5-amino-2,3-dihydrothiophene;
2-(3-nitrophenyl)-3-oxo-4-(3-iodophenyl)-5-amino-2,3-dihydrothiophene;
2-(2,3-dichlorophenyl)-3-oxo-4-(3-trifluoromethylphenyl)-5-amino-2,3-dihydrothiophene;
2-(1-naphthyl)-3-oxo-4-(3-methoxyphenyl)-5-amino-2,3-dihydrothiophene;
2-(3-chloro-8-fluoronaphth-1-yl-3-oxo-4-(3-trifluoromethylphenyl)-5-amino-2,3-dihydrothiophene;
2-(2-trifluoromethyl-3-methyl-8-methoxy-naphth-1-yl)-3-oxo-4-(3-trifluoromethylphenyl)-5-amino-2,3-dihydrothiophene;
2-inden-1 -yl-3-oxo-4-(3-trifluoromethylphenyl)-5-amino-2,3-dihydrothiophene; and
2-(2-fluoroinden-1-yl)-3-oxo-4-(3-trifluoromethylphenyl)-5-amino-2,3-dihydrothiophene.

EXAMPLE 2

(3-Trifluoromethylphenyl)-(2-methylthiopropionyl)-acetonitrile

In this example 6.0 g of (3-trifluoromethylphenyl)-(methylthioacetyl)-acetonitrile in 15 ml of tetrahydrofuran was added dropwise to 43.96 ml of a 1 molar solution of lithium bis(trimethylsilyl)amide, i.e. $[(CH_3)_3Si]_2N^{\ominus}Li^{\oplus}$, under anhydrous conditions at $-70°$ C. The temperature of the resulting mixture was allowed to rise to room temperature and it was then stirred at room temperature for 45 minutes. 3.12 g of methyl iodide was then slowly added and the resulting mixture stirred overnight (about 12–16 hours) under a nitrogen atmosphere. The mixture was added to 200 ml of saturated ammonium chloride solution and then extracted three times with ethyl ether. The ether extracts were combined, dried over magnesium sulfate and concentrated in vacuo yielding a crude oily residue. The residue was chromatographed on silica gel eluting with 70:30 vol. hexane:ethyl acetate yielding 2.9 g of the title compound as an oil.

Similarly, by following the same procedure using the appropriately substituted phenyl-(methylthioacetyl)-acetonitrile and the appropriate R iodide, the corresponding starting materials for Example 3, hereinbelow, can be prepared.

EXAMPLE 2A (3-Trifluoromethylphenyl)-(2-phenyl-2-methylthiopropionyl)-acetonitrile In this example a mixture containing 12 g of (3-trifluoromethylphenyl)-acetonitrile and 14 g of methyl alpha-thiomethylphenylacetate was added to a stirred slurry at room temperature containing 3.4 g of sodium hydride in 150 ml of tetrahydrofuran. The mixture was stirred for 1½ hours at room temperature under a nitrogen atmosphere. The mixture was then added to 250 ml of water extracted twice with ether. The organic (THF+ether) layer was then washed twice with water. The aqueous layers were combined and then acidified to pH 1 with 10% hydrochloric acid, extracted three times with ether, washed with saturated aqueous sodium bicarbonate solution, dried over magnesium sulfate and evaporated under vacuum affording 6.5 g of the title compound as a brown oil.

Similarly, by following the same procedure using the correspondingly substituted starting materials the starting materials for the product listed in Example 3A hereinbelow can be made.

EXAMPLE 3

2-Methyl-3-oxo-4-(3-trifluoromethylphenyl)-5-amino-2,3-dihydrothiophene

In this example, about 2.0 ml of concentrated (98 wt %) sulfuric acid was added to a mixture containing 2.9 g of (3-trifluoromethylphenyl)-(2-methylthiopropionyl)-acetonitrile in 20 ml of acetic acid at room temperature. The mixture was then warmed to reflux and refluxed for thirty minutes. The mixture was then concentrated by evaporation under vacuum. The concentrate was then chromatographed over silica gel eluting with a mixture of 2%, vol., acetone in methylene chloride affording 0.85 g of the title compound.

Similarly, by following the same procedure using the corresponding appropriately substituted starting materials the following compounds can be prepared:
2-ethyl-3-oxo-4-(3-trifluoromethylphenyl)-5-amino-2,3-dihydrothiophene;
2-vinyl-3-oxo-4-(3-trifluoromethylphenyl)-5-amino-2,3-dihydrothiophene;
2-(n-propyl)-3-oxo-4-(3-trifluoromethylphenyl)-5-amino-2,3-dihydrothiophene;
2-(n-butyl)-3-oxo-4-(3-trifluoromethylphenyl)-5-amino-2,3-dihydrothiophene;
2-allyl-3-oxo-4-(2-methoxy-3-trifluoromethylphenyl)-5-amino-2,3-dihydrothiophene;
2-trifluoromethyl-3-oxo-4-(3-trifluoromethylphenyl)-5-amino 2,3-dihydrothiophene;
2-chlorovinyl)-3-oxo-4-(5-nitro-3-trifluoromethylphenyl)-3-oxo-5-amino-2,3-dihydrothiophene;
2-methyl-3-oxo-4-(2-methoxy-3-chlorophenyl)-5-amino-2,3-dihydrothiophene;
2-(n-propyl)-3-oxo-4-(3-difluoromethoxyphenyl)-5-amino-2,3-dihydrothiophene;
2-methyl-3-oxo-4-(3-difluoromethoxyphenyl)-5-amino-2,3-dihydrothiophene;
2-ethyl-3-oxo-4-(2-chloro-3-fluorophenyl)-5-amino-2,3-dihydrothiophene;
2-vinyl-3-oxo-4-(3-propoxyphenyl)-5-amino-2,3-dihydrothiophene;
2-allyl-3-oxo-4-(3-butylthiophenyl)-5-amino-2,3-dihydrothiophene;
2-trifluoromethyl-3-oxo-4-(3-trifluoromethyl-4-bromophenyl)-5-amino-2,3-dihydrothiophene;
2-(2-chlorovinyl)-3-oxo-4-(3-chloromethylthio-4-methylphenyl)-3-oxo-5-amino-2,3-dihydrothiophene;
2-methyl-3-oxo-4-[3-(4-fluorobutyl)phenyl]-5-amino-2,3-dihydrothiophene;
2-ethyl-3-oxo-4-(3-chlorophenyl)-5-amino-2,3-dihydrothiophene;

2-vinyl-3-oxo-4-(3-butylphenyl)-5-amino-2,3-dihydrothiophene;
2-allyl-3-oxo-4-(3-trifluoromethylphenyl)-5-amino-2,3-dihydrothiophene;
2-trifluoromethyl-3-oxo-4-(3,4-difluorophenyl)-5-amino-2,3-dihydrothiophene;
2-ethyl-3-oxo-4-(2-chloro-3-fluorophenyl)-5-amino-2,3-dihydrothiophene;
2-vinyl-3-oxo-4-(2-nitro-3-butoxyphenyl)-5-amino-2,3-dihydrothiophene;
2-allyl-3-oxo-4-(2-methyl-3-trifluoromethyl-phenyl)-5-amino-2,3-dihydrothiophene;
2-(trifluoromethyl)-3-oxo-4-(3-trifluoromethyl-4-bromophenyl)-5-amino-2,3-dihydrothiophene;
2-(2-chlorovinyl)-3-oxo-4-(3-nitro-3-propylphenyl 3-oxo-5-amino-2,3-dihydrothiophene;
2-hexyl-3-oxo-4-(3-fluoromethylthiophenyl)-5-amino-2,3-dihydrothiophene;
2-propyl-3-oxo-4-(3-iodophenyl)-3-oxo-5-amino-2,3-dihydrothiophene;
2-isopropyl-3-oxo-4-(2-chloro-3-fluorophenyl)-5-amino-2,3-dihydrothiophene;
2-ethyl-3-oxo-4-(3-difluoromethoxyphenyl)-5-amino-2,3-dihydrothiophene;
2-cyclohexyl-3-oxo-4-(3-trifluoromethylphenyl)-5-amino-2,3-dihydrothiophene;
2-(2-trifluoromethylbenzyl)-3-oxo-4-(3-tri-fluoromethylphenyl)-5-amino-2,3-dihydrothiophene;
2-(beta-naphth-1-ylethyl)-3-oxo-4-(3-trifluoromethylphenyl)-5-amino-2,3-dihydrothiophene;
2-(2-fluoro-3-2',2'-dichloroethylbenzyl)-3-oxo-4-(3-trifluoromethylphenyl)-5-amino-2,3-dihydrothiophene;
2-(2,3-dichloro-6-methylbenzyl)-3-oxo-4-(3-trifluoromethylphenyl)-5-amino-2,3-dihydrothiophene;
2-(beta-phenethyl)-3-oxo-4-(3-trifluoromethylphenyl)-5-amino-2,3-dihydrothiophene;
2-[3-(2-bromophenyl)propyl]-3-oxo-4-(3-tri-fluoromethylphenyl)-5-amino-2,3-dihydrothiophene;
2-[1-methyl-2-(phenyl)ethyl]-3-oxo-4-(3-tri-fluoromethylphenyl)-5-amino-2,3-dihydrothiophene;
2-naphth-1-ylmethylene-3-oxo-4-(3-trifluoromethylphenyl)-5-amino-2,3-dihydrothiophene;
2-(2-fluoronaphth-1-ylmethylene)-3-oxo-4-(3-trifluoromethylphenyl)-5-amino-2,3-dihydrothiophene;
2-cyclopropylmethylene-3-oxo-4-(3-trifluoromethylphenyl)-5-amino-2,3-dihydrothiophene;
2-(3-butylnaphth-1-ylmethylene)-3-oxo-4-(3-trifluoromethylphenyl)-5-amino-2,3-dihydrothiophene;
2-(5-methoxynaphth-1-ylmethylene)-3-oxo-4-(3-trifluoromethylphenyl)-5-amino-2,3-dihydrothiophene;
2-(6-nitronaphth-1-ylmethylene)-3-oxo-4-(3-trifluoromethylphenyl)-5-amino-2,3-dihydrothiophene;
2-(7-trifluoromethylnaphth-1-ylomethylene)-3-oxo-4-(3-trifluoromethylphenyl)-5-amino-2,3-dihydrothiophene;
2-(2-chloro-8-methylnaphth-1-ylmethylene)-3-oxo-4-(3-trifluoromethylphenyl)-5-amino-2,3-dihydrothiophene;
2-[beta-(8-fluoronaphth-1-yl)ethyl]-3-oxo-4-(3-trifluoromethylphenyl)-5-amino-2,3-dihydrothiophene;
2-[1-(7-methoxynaphth-1-yl)ethyl]-3-oxo-4-(3-trifluoromethylphenyl)-5-amino-2,3-dihydrothiophene;
2-inden-1-ylmethylene-3-oxo-4-(3-trifluoromethylphenyl)-5-amino-2,3-dihydrothiophene;
2-(2-fluoroinden-1-ylmethylene)-3-oxo-4-(3-tri-fluoromethylphenyl)-5-amino-2,3-dihydrothiophene;
2-methoxymethylene-3-oxo-4-(3-trifluoromethylphenyl)-5-amino-2,3-dihydrothiophene;
2-cyclopentylethylene-3-oxo-4-(3-trifluoromethylphenyl)-5-amino-2,3-dihydrothiophene;
2-propoxymethylene-3-oxo-4-(3-trifluoromethylphenyl)-5-amino-2,3-dihydrothiophene;
2-ethoxymethylene-3-oxo-4-(3-trifluoromethylphenyl)-5-amino-2,3-dihydrothiophene;
2-(2-methoxypropyl)-3-oxo-4-(3-trifluoromethylphenyl-2,3-dihydrothiophene;
2-methylthiomethylene-3-oxo-4-(3-trifluoromethylphenyl)-5-amino-2,3-dihydrothiophene; and
2-(1-propylthioethyl)-3-oxo-4-(3-trifluoromethylphenyl)-5-amino-2,3-dihydrothiophene.

EXAMPLE 3A

2-Phenyl-3-oxo-4-(3-trifluoromethylphenyl)-5-amino-2,3-dihydrothiophene

In this example a mixture containing 10.8 g of (3-trifluoromethylphenyl)-(2-phenyl-2-methylthiopropionyl)-acetonitrile and 10 ml of concentrated sulfuric acid in 50 ml of acetic acid is warmed to reflux and refluxed for 20 minutes. The mixture was then concentrated under vacuum thereby removing most of the acetic acid. The concentrate was added to ethyl acetate, washed twice with 1N aqueous sodium hydroxide, then twice with saturated aqueous sodium bicarbonate, and dried over magnesium sulfate. The dried mixture was concentrated by vacuum evaporation affording 7 g of a crude dark oil of the title compound. The crude oil was chromatographed eluting within 1:1 by vol. of hexane:ethyl acetate, affording 1.6 g of the title compound.

Similarly, by following the same procedure using the corresponding starting materials the following compounds can be prepared:
2-methoxy-3-oxo-4-(3-trifluoromethylphenyl)-5-amino-2,3-dihydrothiophene;
2-(3,4-dichlorophenyl)-3-oxo-4-(3-trifluoromethylphenyl)-5-amino-2,3-dihydrothiophene;
2-naphthyl-3-oxo-4-(3-trifluoromethyl-4-bromophenyl)-5-amino-2,3-dihydrothiophene;
2-(3-methylbenzylphenyl)-3-oxo-4-(3-methoxy-4-methylphenyl)-3-oxo-5-amino-2,3-dihydrothiophene;
2-(3-fluorophenyl)-3-oxo-4-(3-chlorophenyl)-5-amino-2,3-dihydrothiophene;
2-(2-fluorobenzyl)-3-oxo-4-(3-methylphenyl)-5-amino-3-dihydrothiophene;
2-(3-chlorobenzyl)-3-oxo-4-(3-butylthiophenyl)-5-amino-2,3-dihydrothiophene;
2-phenyl-3-oxo-4-(3-beta-chloroethylphenyl)-5-amino-2,3-dihydrothiophene;
2-methoxy-3-oxo-4-(3-trifluoromethylphenyl)-5-amino-2,3-dihydrothiophene;
2-n-butoxy-3-oxo-4-(3-trifluoromethylphenyl)-5-amino2,3-dihydrothiophene;
2-(1-naphthyl)-3-4-(3-methoxyphenyl)-5-amino-2,3-dihydrothiophenyl;
2-(3-chloro-8-fluoronaphth-1-yl)-3-oxo-4-(3-tri-fluoromethylphenyl-5-amino-2,3-dihydrothiophene;
2-(2-trifluoromethyl-3-methyl-8-methoxynaphth-1-yl)-3-oxo-4-(3-trifluoromethylphenyl)-5-amino-2,3-dihydrothiophene;
2-inden-1-yl-3-oxo-4-(3-trifluoromethylphenyl)-5-amino-2,3-dihydrothiophene;
2-(2-fluoroinden-1-yl)-3-oxo-4-(3-trifluoromethylphenyl)-5-amino-2,3-dihydrothiophene;
2-(2-chloro-3-propylphenyl)-3-oxo-4-(3-tri-fluoromethylphenyl-5-amino-2,3-dihydrothiophene;

2-(2-nitro-3-methoxyphenyl)-3-oxo-4-(3-tri-fluoromethylphenyl)-5-amino-2,3-dihydrothiophene; and
2-(3-methoxy-5-nitro-7-fluoromethylnaphth-1-yl)-3-oxo-4-(3-trifluoromethylphenyl)-5-amino-2,3-dihydrothiophene;

Example 4

2-Phenyl-3-oxo-4-(-3-trifluoromethylphenyl)-5-methylamino-2,3-dihydrothiophene

This example illustrates a procedure which can be used to prepare the substituted amine derivatives of the present invention.

In this example about 1 g of solid sodium hydroxide in 4.0 ml of water is added to a mixture containing 4.6 g of 2-phenyl-3-oxo-4-(3-trifluoromethylphenyl)-5-amino-1,2-dihydrothiophene in 80 ml of methylene chloride at room temperature followed by the addition of 1.73 g of dimethyl sulfate and 0.21 g of benzyltriethyl ammonium chloride. The resulting two-phase mixture was stirred at room temperature for about 18 hours and was then washed three times with water, dried over magnesium sulfate and then concentrated by evaporation under vacuum. The residue was purified by chromatography over silica gel eluting with 1%, vol., tetrahydrofuran in chloroform affording 1.8 g of the title compound.

Similarly, by following the same procedure using the products listed in Examples 1 and 3 as starting materials, the corresponding 5-methylamino homologs thereof can be prepared, for example:

2-phenyl-3-oxo-4-(5-chloro-3-trifluoromethylphenyl)-5-methylamino-2,3-dihydrothiophene;
2-phenyl-3-oxo-4-(4-chloro-3-trifluoromethylphenyl)-5-methylamino-2,3-dihydrothiophene;
2-phenyl-3-oxo-4-(2-bromo-3-trifluoromethylphenyl)-5-methylamino-2,3-dihydrothiophene;
2-phenyl-3-oxo-4-(6-fluoro--3-trifluoromethylphenyl)-5-methylamino-2,3-dihydrothiophene;
2-phenyl-3-oxo-4-(4-methyl-3-trifluoromethylphenyl)-5-methylamino-2,3-dihydrothiophene;
2-phenyl-3-oxo-4-(5-methoxy-3-trifluoromethylphenyl)-5-methylamino-2,3-dihydrothiophene;
2-phenyl-3-oxo-4-(6-iodo-3-trifluoromethylphenyl)-5-methylamino-2,3-dihydrothiophene;
2-phenyl-3-oxo-4-(3,5-di-trifluoromethylphenyl)-5-methylamino-2,3-dihydrothiophene;
2-(2-nitrophenyl)-3-oxo-4-(3-trifluoromethylphenyl)-5-methylamino-2,3-dihydrothiophene;
2-(3-iodophenyl)-3-oxo-4-(3-trifluoromethylphenyl)-5-methylamino-2,3-dihydrothiophene;
2-(naphth-1-yl)-3-oxo-4-(3-trifluoromethylphenyl)-5-methylamino-2,3-dihydrothiophene;
2-(2-methylnaphth-1-yl)-3-oxo-4-(3-trifluoromethylphenyl)-5-methylamino-2,3-dihydrothiophene;
2-(3-ethoxynaphth-1-yl)-3-oxo-4-(3-trifluoromethylphenyl -5-methylamino-2,3-dihydrothiophene;
2-phenyl-3-oxo-4-(3-n-butylphenyl)-5-methylamino-2,3-dihydrothiophene;
2-phenyl-3-oxo-4-(3-n-butoxyphenyl)-5-methylamino-2,3-dihydrothiophene;
2-phenyl-3-oxo-4-(3-trifluoromethylthiophenyl)-5-methylamino-2,3-dihydrothiophene;
2-phenyl-3-oxo-4-(3-difluoromethoxyphenyl)-5-methylamino-2,3-dihydrothiophene;
2-phenyl-3-oxo-4-(3-chloromethylphenyl)-5-methylamino- 2,3-dihydrothiophene;
2-(2-nitrophenyl)-3-oxo-4-(3-bromophenyl)-5-methylamino-2,3-dihydrothiophene;
2-(6-nitronaphth-1-yl)-3-oxo-4-(2-chloro-3-propylphenyl)-1)-5-methylamino-2,3-dihydrothiophene;
2-(naphth-1-yl)-3-oxo-4-(3-bromo-2-ethylphenyl)-5-methylamino-2,3-dihydrothiophene;
2-(naphth-1-yl)-3-oxo-4-(2,3-difluorophenyl)-5-methylamino-2,3-dihydrothiophene;
2-(2,7-difluoronaphth-1-yl)-3-oxo-4-(3-iodo-4-methylphenyl)-5-methylamino-2,3-dihydrothiophene;
2-phenyl-3-oxo-4-(3-chlorophenyl)-5-methylamino-2,3-dihydrothiophene;
2-phenyl-3-oxo-4-[3-(2-fluoropropylthio)phenyl]5methylamino-2,3-dihydrothiophene;
2-phenyl-3-oxo-4-(3-t-butoxyphenyl)-5-methyl-amino-2,3-dihydrothiophene;
2-phenyl-3-oxo-4[3-(2,3-dichloropropylthio-phenyl)-5-methylamino-2,3-dihydrothiophene;
2-phenyl-3-oxo-4-(3-bromophenyl)-5-methylamino-2,3-dihydrothiophene;
2-(2,3-dinitrophenyl)-3-oxo-4-(3-iodophenyl)-5-methylamino- 2,3-dihydrothiophene;
2-(8-trifluoromethylnaphth-1-yl)-3-oxo-4-(3fluorophenyl)-5-methylamino-2,3-dihydrothiophene;
2-(naphth-1-yl)-3-oxo-4-(3-isopropoxyphenyl)-5-methylamino-2,3-dihydrothiophene;
2-(6-butyl-8-chloronaphth-1-yl)-3-oxo-4-(3-fluorophenyl)-5-methylamino-2,3-dihydrothiophene;
2-(3-nitronaphth-1-yl)-3-oxo-4-(3-fluorophenyl)-5-methylamino-2,3-dihydrothiophene;
2-(3-nitrophenyl)-3-oxo-4(3-iodophenyl)-5-methylamino-2,3-dihydrothiophene;
2-(2,3-dichlorophenyl)-3-oxo-4-(3-trifluoromethylphenyl)-5-methylamino-2,3-dihydrothiophene;
2-(1-naphthyl)-3-oxo-4-(3-methoxyphenyl)-5-methylamino-2,3-dihydrothiophene;
2-(3-chloro-8-fluoronaphth-1-yl)-3-oxo-4-(3-trifluoromethylphenyl)-5-methylamino-2,3-dihydrothiophene;
2-(2-trifluoromethyl-3-methyl-8-methoxy-naphth-1yl)-(3-oxo-4-(3-trifluoromethylphenyl)-5-methylamino-2,3-dihydrothhiophene;
2-inden-1-yl-3-oxo-4-(3-trifluoromethylphenyl)-5methylamino 2,3-dihydrothiophene;
2-(2-fluoroinden-1-yl)-3-oxo-4-(3-trifluoromethylphenyl)-5-methylamino-2,3-dihydrothiophene;
2-methyl-3-oxo-4-(3-trifluoromethylphenyl)-5-methylamino-2,3-dihydrothiophene;
2-ethyl-3-oxo-4-(3-trifluoromethylphenyl)-5-methylamino-2,3-dihydrothiophene;
2-ethyl-3-oxo-4-(3-difluoromethoxyphenyl)-5-methylamino-2,3-dihydrothiophene;
2-(n-propyl-3-oxo-4-(3-difluoromethoxyphenyl)-5-methylamino2,3-dihydrothiophene;
2-vinyl3-oxo-4-(3-trifluoromethylphenyl)-5-methylamino-2,3-dihydrothiophene;
2-(n-propyl)-3-oxo-4-(3-trifluoromethylphenyl)-5-methylamino-2,3-dihydrothiophene;
2-(n-butyl)-3-oxo-4-(3-trifluoromethylphenyl)-5-methylamino-2,3-dihydrothiophene;
2-allyl-3-oxo-4-(2-methoxy-3-trifluoromethylphenyl)-5-methylamino-2,3-dihydrothiophene;
2-trifluoromethyl-3-oxo-4-(3-trifluoromethylphenyl)-5-methylamino-2,3-dihydrothiophene;
2-(2-chlorovinyl)-3-oxo-4-(5-nitro-3-trifluoromethylphenyl)-3-oxo-5-methylamino-2,3-dihydrothiophene;
2-methyl-3-oxo-4-(2-methoxy-3-chlorophenyl)-5-methylamino-2,3-dihydrothiophene;

2-ethyl-3-oxo-4-(2-chloro-3-fluorophenyl)-5-methylamino-2,3-dihydrothiophene;
2-vinyl-3-oxo-4-(3-propoxyphenyl)-5-methylamino-2,3-dihydrothiophene;
2-methyl-3-oxo-4-(3-difluoromethoxyphenyl)-5-methylamino-2,3-dihydrothiophene;
2-allyl-2,3-oxo-4-(3-butylthiophenyl)-5-methylamino-2,3-dihydrothiophene;
2-trifluoromethyl-3-oxo-4-(3-trifluoromethyl-4-bromophenyl)-5-methylamino-2,3-dihydrothiophene;
2-(2-chlorovinyl)-3-oxo-4-(3-chloromethylthio-4-methylphenyl)-3-oxo-5-methylamino-2,3-dihydrothiophene;
2-methyl-3-oxo-4-[3-(4-fluorobutyl)phenyl]-5-methylamino-2,3-dihydrothiophene;
2-ethyl-3-oxo-4-(3-chlorophenyl)-5-methylamino-2,3-dihydrothiophene;
2-vinyl-3-oxo-4-(3-butylphenyl)-5-methylamino-2,3-dihydrothiophene;
2-allyl-3-oxo-4-(3-trifluoromethylphenyl)-5-methylamino-2,3-dihydrothiophene;
2-trifluoromethyl-3-oxo-4-(3,4-difluorophenyl)-5-methylamino-2,3dihydrothiophene;
2-(2-chlorovinyl)-3-oxo-4-(3-bromophenyl)-3-oxo-5-methylamino-2,3-dihydrothiophene;
2-cyclopropylmethylene-3-oxo-4-(3-trifluoromethylphenyl)-5-methylamino-2,3-dihydrothiophene;
2-cyclopentylethylene-3-oxo-4-(3-trifluoromethylphenyl)-5-methylamino-2,3-dihydrothiophene;
2-methyl-3-oxo-4-(2-methoxy-3-chlorophenyl)-5-methylamino-2,3-dihydrothiophene;
2-ethyl-3-oxo-4-(2-chloro-3-fluorophenyl)-5-methylamino-2,3-dihydrothiophene;
2-vinyl-3-oxo-4-(2-nitro-3-butoxyphenyl)-5-methylamino-2,3-dihydrothiophene;
2-allyl-3-oxo-4-(2-methyl-3-trifluoromethylphenyl)-5-methylamino-2,3-dihydrothiophene;
2-(trifluoromethyl)-3-oxo-4-(3-trifluoromethyl)-4-bromophenyl)-5-methylamino-2,3-dihydrothiophene;
(2-chlorovinyl)-3-oxo-4-(3-nitro-3-propylpheny-)-3-oxo-5-methylamino-2,3-dihydrothiophene;
2-hexyl-3-oxo-4-(3-fluoromethylthiophenyl)-5methylamino-2,3-dihydrothiophene;
2-propyl-3-oxo-4-(3-iodophenyl)-3-oxo-5-methylamino-2,3-dihydrothiophene;
2-isopropyl-3-oxo-4-(2-chloro-3-fluorophenyl)-5-methylamino-2,3-dihydrothiophene;
2-cyclohexyl-3-oxo-4-(3-trifluoromethylphenyl)-5-methylamino- 2,3-dihydrothiophene;
2-(2-trifluoromethylbenzyl)-3-oxo-4-(3-trifluoromethylphenyl)-5-methylamino-2,3-dihydrothiophene;
2-(beta-naphth-1-ylethyl)-3-oxo-4-(3-trifluoromethylphenyl)-5-methylamino-2,3-dihydrothiophene;
2-(2-fluoro-3-2',2'-dichloroethylbenzyl)-3-oxo-4-(3-trifluoromethylphenyl)-5-methylamino-2,3-dihydrothiophene;
2-(2,3-dichloro-6-methylbenzyl)-3-oxo-4-(3-trifluoromethylphenyl)-5-methylamino-2,3-dihydrothiophene;
2-(beta-phenethyl)-3-oxo-4-(3-trifluoromethylphenyl)-5-methylamino-2,3-dihydrothiophene;
2-[3-(2-bromophenyl)propyl]-3-oxo-4-(3-trifluoromethylpnenyl)-5-methylamino-2,3-dihydrothiophene;
2-[1-methyl-2-(phenyl)ethyl]-3-oxo-4-(3-trifluoromethylphenyl)-5-methylamino-2,3-dihydrothiophene;
2-naphth-1-ylmethylene-3-oxo-4-(3-trifluoromethylphenyl)-5-methylamino-2,3-dihydrothiophene;
(2-fluoronaphth-1-ylmethylene)-3-oxo-4-(3-trifluoromethylphenyl)-5-methylamino-2,3-dihydrothiophene;
2-(3-butylnaphth-1-ylmethylene)-3-oxo-4-(3-trifluoromethylphenyl)-5-methylamino-2,3-dihydrothiophene;
(5-methoxynaphth-1-ylmethylene)-3-oxo-4-(3-trifluoromethylphenyl)-5-methylamino-2,3-dihydrothiophene;
2-(6-nitronaphth-1-ylmethylene)-3-oxo-4-(3-trifluoromethylphenyl)-5-methylamino-2,3-dihydrothiophene;
(7-trifluoromethylnaphth-1-ylomethylene)-3-oxo-4-(3-trifluoromethylphenyl)-5-methylamino-2,3-dihydrothiophene;
2-(2-chloro-8-methylnaphth-1-ylmethylene)-3-oxo-4-(3-trifluoromethylphenyl)-5-methylamino-2,3-dihydrothiophene;
2-[beta-(8-fluoronaphth-1-yil)ethyl]-3-oxo-4-(3-trifluoromethylphenyl)-5-methylamino-2,3-dihydrothiophene;
2-[1-(7-methoxynaphth-1-yl)ethyl]-3-oxo-4-(3-trifluoromethylphenyl)-5-methylamino-2,3-dihydrothiophene;
2-inden-1-ylmethylene-3-oxo-4-(3-trifluoromethylphenyl)-5-methylamino-2,3-dihydrothiophene;
2-(2-fluoroinden-1-ylmethylene)-3-oxo-4-(3-trifluoromethylphenyl-5-methylamino-2,3-dihydrothiophene;
2-methoxymethylene-3-oxo-4-(3-trifluoromethylphenyl-5-methylamino-2,3-dihydrothiophene;
2-propoxymethylene-3-oxo-4-(3-trifluoromethylphenyl)-5-methylamino-2,3-dihydrothiophene;
2-ethoxymethylene-3-oxo-4-(3-trifluoromethylpheny)-5methylamino-2,3-dihydrothiophene;
2-(2-methoxypropyl)-3-oxo-4-(3-trifluoromethylphenyl)-5-methylamino-2,3-dihydrothiophene;
2-methylthiomethylene-3-oxo-4-(3-trifluoromethylphenyl)-5-methylamino-2,3-dihydrothiophehe; and
2-(1-propylthioethyl)-3-oxo-4-(3-trifluoromethylphenyl)-5-methylamino-2,3-dihydrothiophene.
2-(3,4-dichlorophenyl)-3-oxo-4-(3-trifluoromethylphenyl)-5-methylamino-2,3-dihydrothiophene;
2-naphthyl-3-oxo-4-(3-trifluoromethyl-4-bromomethyl-5-methylamino-2,3-dihydrothiophene;
2-(3-methylbenzylphenyl)-3-oxo-4-(3-methoxy-4-methylphenyl)-3-oxo-5-methylamino-2,3-dihydrothiophene;
2-(3-fluorophenyl)-3-oxo-4-(3-chlorophenyl)-5-methylamino-2,3-dihydrothiophene;
2-(2-fluorobenzyl)-3-oxo-4-(3-methylphenyl)-5-methylamino-2,3-dihydrothiophene;
2-(3-chlorobenzyl)-3-oxo-4-(3-butylthiophenyl)-5-methylamino-2,3-dihydrothiophene;
2-phenyl-3-oxo-4-(3-beta-chloroethylphenyl)-5-methylamino-2,3-dihydrothiophene;
2methoxy-3-oxo-4(3trifluoromethylphenyl)-5-methylamino-2,3-dihydrothiophene;
2-n-butoxy-3-oxo-4-(3-trifluoromethylphenyl)-5-methylamino-2,3-dihydrothiophene;
2-(1-naphthyl)-3-4-(3-methoxyphenyl)-5-methylamino-2,3-dihydrothiophene;
2-(3-chloro-8-fluoronaphth-1-yl)-3-oxo-4-(3-trifluoromethylphenyl)-5-methylamino-2,3-dihydrothiophene;
2-(2-trifluoromethyl-3-methyl-8-methoxynaphth-1-yl)-3-oxo-4-(3-trifluoromethylphenyl)-5-methylamino-2,3-dihydrothiophene;

2-inden-1-yl-3-oxo-4-(3-trifluoromethylphenyl)-5-methylamino-2,3-dihydrothiophene;

2-(2-fluoroinden-1-yl)-3-oxo-4-(3-trifluoromethylphenyl)-5-methylamino-2,3-dihydrothiophene;

2-(2-chloro-3-propylphenyl)-3-oxo-4-(3-trifluoromethylphenyl-5-methylamino-2,3-dihydrothiophene;

2-(2-nitro-3-methoxyphenyl)-3-oxo-4-(3-trifluoromethylphenyl)-5-methylamino-2,3-dihydrothiophene; and 2-(3-methoxy-5-nitro-7-fluoromethylnaphth-1-yl)-3-oxo-4-(3-trifluoromethylphenyl)-5-methylamino-2,3-dihydrothiophene;

Similarly, by approximately doubling the amount of dimethylsulfate and increasing the reaction time, the corresponding 5-dimethylamino homologs thereof can be prepared. By using diethylsulfate in place of dimethylsulfate the corresponding 5-ethylamino and 5-diethylamino homologs of the above compounds can be prepared.

Example 5

2-Fluorophenyl)-3-oxo-4-(3-trifluoromethylphenyl)-5-allylamino-2,3-dihydrothiophene This example illustrates a general procedure which can be used to prepare 5-substituted amino compounds of the present invention.

One gram of sodium hydroxide in 4.0 ml of water is added to a mixture of 4.0 g of 2-(2-fluorophenyl)-3-oxo-4-(3-trifluoromethylphenyl)-5-amino-1,2-dihydrothiophene in 80 ml of methylene chloride at room temperature followed by the addition of 1.37 g of allyl bromide and 0.27 g of benzyltriethylammonium chloride. This will result in a two-phase mixture. The mixture is stirred at room temperature for about 18 hours after which time it is washed three times with water, dried over magnesium sulfate and concentrated in vacuo. The residue can be purified by chromatography over silica gel to yield the title compound.

Similarly, by applying this procedure to the products listed in Examples 1 and 2, the corresponding 5-allylamino analogs thereof can be prepared. Similarly, by approximately doubling the amount of allyl bromide and sodium hydroxide, the corresponding 5-diallylamino analogs thereof can be prepared.

In a like manner, by using ethyl bromide in place of allyl bromide, the corresponding 5-ethyl and 5-diethyl analogs can be prepared.

Similarly, by following the same procedure by respectively using methoxymethyl bromide, ethylthiomethyl bromide, methyl bromoacetate, methyl 2-bromobutyrate, 1,5-dibromopentane, and cis-1,4-dibromobut-1,3-diene in place of alkyl bromide the corresponding 5-methoxymethylamino, 5-ethyilthiomethylamino, 5-methoxycarbonylmethylamino, 5-(1-methoxycarbonyl propylamino), 5-piperidin-1-yl and 5-pyrrol-1-yl analogs of the products llisted in Examples 2,3 and 6 can be prepared for example:

2-phenyl-3-oxo-4-(3-trifluoromethylphenyl)-5-methoxymethylamino-2,3-dihydrothiophene;

2-methyl-3-oxo-4-(3-trifluoromethylphenyl)-5-methoxymethylamino-2,3-dihydrothiophene;

2-ethyl-3-oxo-4-(3-trifluoromethylphenyl)-5-methoxymethylamino-2,3-dihydrothiophene;

2-phenyl-3-oxo4-(3-trifluoromethylphenyl)-5-ehtylthiomethylamino-2,3-dihydrothiophene;

2-methoxy-3-oxo-4-(3-trifluoromethylphenyl)-5-ethylthiomethylamino- 2,3-dihydrothiophene;

2-methyl-3-oxo-4-(3-trifluoromethylphenyl)-5-ethylthiomethylamino-2,3-dihydrothiophene;

2-ethoxymethylene-3-oxo-4-(3-trifluoromethylphenyl)5-ethylthiomethylamino-2,3-dihydrothiophene;

2-ethyl-3-oxo-4-(3-trifluoromethylphenyl)-5-ethylthiomethylamino-2,3-dihydrothiophene;

2-phenyl-3-oxo-4-(3-trifluoromethylphenyl)-5-methoxycarbonylmethylamino-2,3-dihydrothiophene;

3-methyl-3-oxo-4-(3-trifluoromethylphenyl)-5-methoxycarbonylmethylamino-2,3-dihydrothiophene;

2-methylthiomethylene-3-oxo-4-(3-trifluoromethylphenyl-1)-5-methoxycarbonylmethylamino-2,3-dihydrothiophene;

2-ethyl-3-oxo-4-(3-trifluoromethylphenyl)-5-methoxycarbonylmethylamino-2,3-dihydrothiophene;

2-phenyl-3-oxo-4-(3-trifluoromethylphenyl)-5-(1-methoxycarbonylprop-1-yl)amino-2,3-dihydrothiophene;

2-methyl-3-oxo-4-(3-trifluoromethylphenyl)-5-(1-methoxycarbonylprop-1-yl)amino-2,3-dihydrothiophene;

2-fluoro-3-oxo-4-(3-trifluoromethylphenyl)-5-(1-methoxylcarbonylprop-1-yl)amino-2,3-dihydrothiophene;

2-ethyl-3-oxo-4-(3-trifluoromethylphenyl)-5-(1-methoxycarbonylprop-1-yl)amino-2,3-dihydrothiophene;

2-naphth-1-yl-3-oxo-4-(3-trifluoromethylphenyl)-(1-methoxycarbonylprop-1-yl)amino-2,3-dihydrothiophene;

2-inden-1-yl-3-oxo-4-(3-trifluoromethylphenyl)-(1-methoxycarbonylprop-1-yl)amino-2,3-dihydrothiophene;

2-phenyl-3-oxo-4-(3-trifluoromethylphenyl)-5-piperidin-1-yl-2,3-dihydrothiophene; and 2-phenyl-3-oxo-4-(3-trifluoromethylphenyl)-5-pyrroll-yl-2,3-dihydrothiophene, etc.

Similarly, by applying the above procedures using the 5-methylamino products of Example 4 as starting materials, the corresponding 5-(N-methyl-N-allylamino), 5-(N-methyl-(N-methyl-N-ethylamino), 5-(N-methyl-N-methoxymethylamino), 5-(N-methyl-N-ethylthiomethylamino), 5-(N-methyl-N-methoxycarbonylmethylamino), and 5-(N-methyl-N-1'-methoxycarbonylpropylamino) analogs can be prepared.

Example 6

2-Phenyl-3-oxo-4-(3-trifluoromethylphenyl)-5-amino-2,3-dihydrothiophene oxide

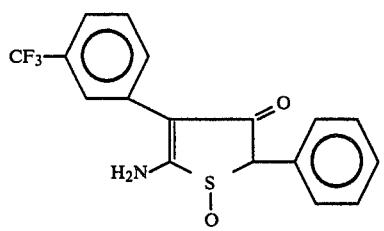

In this example 1.75 g of 2-phenyl-3-oxo-4-(3-trifluoromethylphenyl)-5-amino-1,2-dihydrothiophene was dissolved in 35 ml of methylene chloride at room temperature. To the resulting solution was admixed dropwise a solution of 1.53 g of 80% m-chloroperbenzoic acid in 35 ml of methylene chloride. The reaction mixture was stirred overnight (about 18 hours) at room temperature after which time it was washed three times with aqueous sodium thiosulfate solution, one time with 1N hydrochloric acid, one time with water, one time with saturated aqueous sodium bicarbonate and one time with brine. The organic phase was dried over magnesium sulfate and concentrated in vacuo to give 1.86 g of brown foam which was chromatographed on silica eluted with 50/50 petroleum ether/ethylacetate yielding 1.03 g of the title compound.

Similarly, the corresponding dihydrothiophene oxides of the thiophene products listed in Examples 1, 3–5 can be prepared via the same procedure but using the corresponding dihydrothiophenes of Examples 1, 3–5 as starting materials.

Example 6A

2-Phenyl-3-oxo-4-(3-trifluoromethylphenyl)-5-methylamino-2,3-dihydrothiophene dioxide

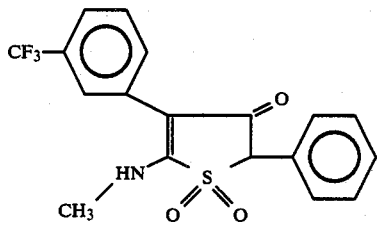

The title compound can be prepared via the starting material described hereinabove in Example 4, using the procedure described in Example 6, but doubling the amount of m-chloroperbenzoic acid.

The corresponding dihydrothiophene dioxide analogs of the products listed in Examples 1 3–5 can be prepared via the same procedure using the corresponding dihydrothiophene starting materials.

Example 7

Lithium salt of 2-phenyl-3-oxo-4-(3-trifluoromethylphenyl)-5-methylamino-2,3-dihydrothiophene This example illustrates a procedure which can be used to prepare the cation salts of the present invention.

In this example, 6.6 ml of 1.6 M n-butyllithium in hexane is added dropwise to a stirred solution containing 2.86 g of 2-methyl-3-oxo-4-(3-trifluoromethylphenyl)-5-amino-2,3-dihydrothiophene in 25 ml of tetrahydrofuran at $-30°$ C. The resulting mixture is stirred for 20 minutes and then concentrated in vacuo to afford the title compound Similarly, by following the same procedure, the corresponding lithium salts of the compounds of Examples 1, and 3–5 can also be prepared.

Example 8

The compounds listed in Tables A and B hereinbelow were prepared using the appropriate starting materials in procedures described in the Examples hereinabove. A number of comparison compounds were also prepared using similar procedures. These comparison compounds include among others the reference compounds 5-amino-3-oxo-4-phenyl-2,3-dihydrothiophene; 5-amino-3-oxo-4-(2-fluorophenyl)-2,3-dihydrothiophene and 5-amino-3-oxo-4-(2-chlorophenyl)-2,3-dihydrothiophene. The comparison compounds are reported in Table C hereinbelow.

TABLE A

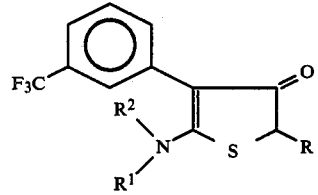

| No. | $R^1$ | $R^2$ | R | Carbon Calc. | Carbon Found | Hydrogen Calc. | Hydrogen Found | Nitrogen Calc. | Nitrogen Found | Melting Point °C. |
|---|---|---|---|---|---|---|---|---|---|---|
| 1 | H | H | $CH_3$ | 52.75 | 53.43 | 3.66 | 4.12 | 5.13 | 5.29 | 46–68 |
| 2 | H | H | $CH_2CH_3$ | 54.36 | 55.06 | 4.18 | 4.39 | 4.88 | 5.03 | 117–121 |
| 3 | H | H | $-CH_2CH_2CH_3$ | 55.81 | 56.13 | 4.65 | 5.22 | 4.65 | 4.84 | 180–182* |
| 4 | H | H | $-CH(CH_3)_2$ | 55.81 | 57.12 | 4.65 | 5.07 | 4.65 | 4.75 | 135–138 |
| 5 | H | H | $-(CH_2)_3CH_3$ | 57.13 | 62.0 | 5.11 | 6.03 | 4.44 | 4.85 | 90.5–103.5 |
| 6 | H | H | $-CH_2CH(CH_3)_2$ | 57.1 | 59.9 | 5.1 | 5.9 | 4.4 | 4.3 | oil |
| 7 | $CH_3$ | H | $CH_3$ | 54.35 | 53.67 | 4.21 | 4.46 | 4.88 | 5.13 | 97–107 |
| 8 | $CH_3$ | H | $-CH_2CH_3$ | 55.80 | 56.39 | 4.68 | 4.92 | 4.65 | 4.86 | 137–139* |
| 9 | $CH_3$ | H | $-CH_2CH_2CH_3$ | 57.13 | 58.44 | 5.11 | 5.36 | 4.44 | 5.32 | oil |
| 10 | $CH_3$ | H | $-CH(CH_3)_2$ | 57.13 | 57.09 | 5.11 | 5.52 | 4.44 | 4.42 | 129.5–136 |
| 11 | $CH_3$ | H | $-(CH_2)_3CH_3$ | 58.34 | 58.43 | 5.51 | 6.05 | 4.25 | 4.48 | 109–112 |
| 12 | $CH_3$ | H | $-CH_2CH(CH_3)_2$ | 58.34 | 56.5 | 5.51 | 5.7 | 4.25 | 4.1 | 88–92 |
| 13 | $-CH_2CH_3$ | H | $CH_3$ | 55.80 | 55.93 | 4.68 | 5.02 | 4.65 | 4.81 | 158–163* |
| 14 | $-CH_2CH_3$ | H | $-CH_2CH_3$ | 57.13 | 56.93 | 5.11 | 5.0 | 4.44 | 4.45 | 138–141* |
| 15 | $-CH_2CH_3$ | H | $-CH_2CH_2CH_3$ | 58.34 | 58.07 | 5.51 | 5.53 | 4.25 | 4.2 | 90–98 |
| 16 | $CH_3$ | $CH_3$ | $CH_3$ | 55.80 | 56.45 | 4.68 | 4.97 | 4.65 | 4.82 | oil |
| 17 | $CH_3$ | $CH_3$ | $-CH_2CH_3$ | 57.13 | 54.36 | 5.11 | 5.21 | 4.44 | 4.59 | oil |
| 18 | $CH_3$ | $CH_3$ | $-CH_2CH_2CH_3$ | 58.34 | 57.77 | 5.51 | 5.76 | 4.25 | 4.14 | oil |
| 19 | $CH_3$ | $CH_3$ | $-CH(CH_3)_2$ | 58.34 | 56.97 | 5.51 | 5.52 | 4.25 | 4.08 | oil |
| 20 | $CH_3$ | $CH_3$ | $-(CH_2)_3CH_3$ | 59.46 | 57.51 | 5.87 | 5.71 | 4.08 | 4.09 | oil |
| 21 | $CH_3$ | $CH_3$ | $-CH_2CH(CH_3)_2$ | 59.46 | 58.9 | 5.87 | 6.1 | 4.08 | 4.0 | oil |
| 22 | $CH_2CH_3$ | $CH_2CH_3$ | $-CH_2CH_2CH_3$ | 60.49 | 59.23 | 6.20 | 6.27 | 3.92 | 4.2 | oil |
| 23 | H | H | $-CH_2CH=CH_2$ | 56.19 | 56.5 | 4.01 | 4.34 | 4.68 | 3.93 | 134–141 |
| 24 | H | H | $-CH_2CH=CHCl$ | 50.38 | 51.38 | 3.30 | 3.9 | 4.20 | 4.18 | 118–121 |

TABLE A-continued

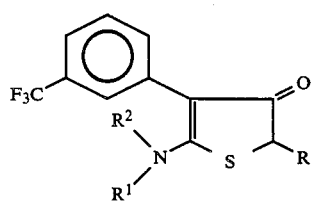

| No. | $R^1$ | $R^2$ | R | Carbon Calc. | Carbon Found | Hydrogen Calc. | Hydrogen Found | Nitrogen Calc. | Nitrogen Found | Melting Point °C. |
|---|---|---|---|---|---|---|---|---|---|---|
| 25 | $CH_3$ | H | $-CH_2CH=CH_2$ | 57.50 | 56.29 | 4.50 | 4.86 | 4.47 | 4.17 | 119.5-128 |
| 26 | $CH_3$ | H | $-CH_2CH=CHCl$ | 51.80 | 51.42 | 3.77 | 3.71 | 4.03 | 3.97 | 79-87 |
| 27 | $CH_3$ | $CH_3$ | $-CH_2CH=CH_2$ | 58.70 | 58.02 | 4.93 | 4.71 | 4.28 | 4.27 | oil |
| 28 | $CH_3$ | $CH_3$ | $-CH_2CH=CHCl$ | 53.11 | 50.66 | 4.18 | 4.29 | 3.87 | 3.33 | oil |
| 29 | H | H | $\phi$** | 60.90 | 61.28 | 3.58 | 3.72 | 4.18 | 3.97 | 142-146 |
| 30 | H | H | $3-CF_3\phi$ | 53.60 | 53.67 | 2.73 | 2.95 | 3.47 | 3.35 | 69-71 |
| 31*** | H | H | $4-F-\phi$ | 57.79 | 56.81 | 3.12 | 3.43 | 4.00 | 3.43 | 84-86 |
| 32 | H | H | $2-CH_3\phi$ | 61.89 | 61.73 | 4.01 | 4.38 | 4.01 | 3.65 | 83-85 |
| 33 | H | H | $3-CH_3O\phi$ | 59.18 | 57.8 | 3.84 | 3.98 | 3.84 | 3.80 | 173-176 |
| 34 | H | H | $2-F\phi$ | 57.79 | 56.93 | 3.12 | 4.03 | 3.97 | 3.64 | 169-171 |
| 35 | H | H | $2-Cl\phi$ | 55.22 | 56.66 | 2.98 | 4.09 | 3.79 | 3.72 | 72-76 |
| 36 | H | H | $3-Cl\phi$ | 55.22 | 55.91 | 2.98 | 3.42 | 3.79 | 4.01 | 138-139 |
| 37 | H | H | H | 51.0 | 51.13 | 3.09 | 3.93 | 5.41 | 5.4 | 141-143 |
| 38 | $CH_3$ | H | H | 52.78 | 54.45 | 3.66 | 3.76 | 5.13 | 5.41 | 103-104 |
| 39 | $CH_3$ | H | $\phi$ | 61.89 | 63.17 | 4.01 | 4.23 | 4.01 | 4.32 | 157-167* |
| 40 | $CH_2CH_3$ | H | $\phi$ | 62.80 | 63.23 | 4.44 | 4.76 | 3.85 | 4.06 | 128-144 |
| 41 | $CH_3$ | $CH_3$ | $\phi$ | 62.81 | 62.89 | 4.41 | 4.37 | 3.86 | 4.16 | 53-68 |
| 42 | $CH_3$ | H | $2-CH_3\phi$ | 62.81 | 60.64 | 4.41 | 4.67 | 3.86 | 3.73 | 81-85 |
| 43 | $CH_2CH_3$ | H | $2-CH_3\phi$ | 63.66 | 63.64 | 4.77 | 5.18 | 3.71 | 3.81 | 55-63 |
| 44 | H | H | $-CH_2\phi$ | 61.89 | 55.65 | 4.01 | 3.76 | 4.01 | 3.14 | 220-222* |
| 45 | H | H | $-CH_2-\triangleleft$ | 57.50 | 57.98 | 4.50 | 4.68 | 4.47 | 4.80 | 109-113.5 |
| 46 | $CH_3$ | H | $-CH_2-\triangleleft$ | 58.70 | 55.73 | 4.93 | 5.32 | 4.28 | 4.05 | 93-100 |
| 47 | $CH_3$ | $CH_3$ | $-CH_2-\triangleleft$ | 59.81 | 57.69 | 5.31 | 5.65 | 4.10 | 3.99 | oil |

\* = Decomposition
$\phi$** = Phenyl, for example, $3-CF_3\phi$ = trifluoromethylphenyl
31*** = This product was only 61% pure.

TABLE B

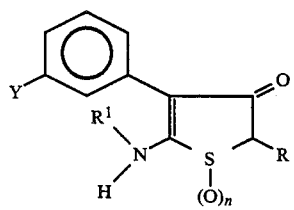

| No. | Y | n | R | $R^1$ | Carbon Calc. | Carbon Found | Hydrogen Calc. | Hydrogen Found | Nitrogen Calc. | Nitrogen Found | Melting Point °C. |
|---|---|---|---|---|---|---|---|---|---|---|---|
| 48 | 3-F | 0 | $CH_3$ | H | 59.19 | 59.48 | 4.48 | 4.65 | 6.28 | 6.11 | 123-125 |
| 49 | 3-Cl | 0 | $CH_3$ | H | 55.13 | 58.73 | 4.18 | 4.84 | 5.85 | 6.11 | 120-122 |
| 50 | 3-Cl | 0 | $\phi$ | H | 63.68 | 64.94 | 4.01 | 4.61 | 4.64 | 4.85 | 155-159 |
| 51 | $3-CF_3$ | 1 | $\phi$ | H | 58.12 | 58.05 | 3.42 | 3.88 | 3.99 | 4.28 | 155-159* |
| 52 | $3-CF_3$ | 1 | $\phi$ | $CH_3$ | 59.17 | 55.80 | 3.86 | 3.82 | 3.83 | 3.46 | foam |
| 53 | $3-CF_3$ | 2 | $\phi$ | $CH_3$ | 56.69 | 56.54 | 3.70 | 3.74 | 3.67 | 3.56 | 77-82 |

\* = Decomposition

TABLE C
COMPARISON COMPOUNDS

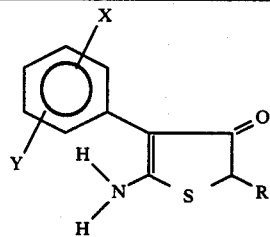

| No. | Y | X | R | Carbon Calc. | Carbon Found | Hydrogen Calc. | Hydrogen Found | Nitrogen Calc. | Nitrogen Found | Melting Point °C. |
|---|---|---|---|---|---|---|---|---|---|---|
| C-1 | H | H | H | 62.82 | 63.03 | 4.71 | 5.11 | 7.33 | 7.18 | 204–205 |
| C-2 | 4-CH$_3$ | H | H | 64.39 | 64.49 | 5.37 | 5.49 | 6.83 | 6.55 | 158–163 |
| C-3 | 2-F | H | H | 57.42 | 57.41 | 3.83 | 4.16 | 6.7 | 6.84 | 195–196* |
| C-4 | 4-Cl | H | H | 53.23 | 54.9 | 3.55 | 3.92 | 6.21 | 6.6 | 176–177 |
| C-5 | 3-Cl | 4-Cl | H | 46.17 | 48.67 | 2.69 | 2.97 | 5.39 | 6.06 | 194–196 |
| C-6 | 2-Cl | H | CH$_3$ | 55.13 | 56.06 | 4.18 | 4.91 | 5.85 | 5.45 | 112–114 |
| C-7 | 2-Cl | H | φ | 63.68 | 63.73 | 4.01 | 4.26 | 4.64 | 4.71 | 185.5–188 |
| C-8 | 3-CH$_3$ | H | φ | 72.57 | 72.57 | 5.37 | 5.66 | 4.98 | 4.96 | 191–195 |
| C-9 | 3-OCH$_3$ | H | φ | 68.66 | 67.43 | 5.08 | 5.34 | 4.71 | 4.68 | 57–67 |
| C-10 | 3-CF$_3$ | H | 4-CH$_3$φ | 61.89 | 62.22 | 4.01 | 4.36 | 4.01 | 3.9 | 65–68 |
| C-11 | 3-CF$_3$ | H | 4-CH$_3$Oφ | 59.18 | 60.37 | 3.84 | 5.82 | 3.84 | 3.88 | 74–76 |
| C-12 | 3-CF$_3$ | H | 4-Clφ | 55.22 | 56.02 | 2.98 | 3.44 | 3.79 | 3.56 | 88–92 |
| C-13 | 3-CF$_3$ | H | 3,4-di(Cl)φ | 50.51 | 51.58 | 2.48 | 3.08 | 3.47 | 3.39 | 83–86 |
| C-14 | H | H | 2,6-Cl$_2$φ | 50.51 | 52.14 | 2.48 | 2.65 | 3.47 | 3.71 | 76–87 |
| C-15 | 3-CF$_3$ | H | CH$_3$ClC≡CHCH$_2$ | 51.81 | 53.04 | 3.74 | 4.15 | 4.03 | 4.04 | 113–119 |
| C-16 | 2-Cl | 4-Cl | φ | 57.15 | 57.58 | 3.30 | 3.73 | 4.17 | 5.25 | 93–97 |

* = Decomposition

Example 9

In this example, the compounds of Tables A and B and the comparison compounds of Table C, hereinabove, were respectively tested using the procedures described herein-below for pre-emergent and post-emergent activity against a variety of grasses and broad-leaf plants including one grain crop and one broad-leaf crop. The compounds tested are identified by compound number in Tables A, B and C hereinabove.

Pre-Emergent Herbicide Test

Pre-emergence herbicidal activity was determined in the following manner.

Test solutions of the respective compounds were prepared as follows:

355 5 mg of test compound was dissolved in 15 ml of acetone. 2 ml of acetone containing 110 mg of a nonionic surfactant was added to the solution. 12 ml of this stock solution was then added to 47.7 ml of water which contained the same nonionic surfactant at a concentration of 625 mg/l. In the case where the test material used is not essentially pure compound the amount of material used is adjusted to provide the desired concentration of compound.

Seeds of the test vegetation were planted in a pot of soil and the test solution was sprayed uniformly onto the soil surface either at a dose of 27.5 micrograms/cm$^2$ or in some instances as indicated in Table 1 hereinbelow, certain of the compounds were tested at a lower dosages. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests are summarized in Table 1.

Post-Emergent Herbicidal Test

The test compound was formulated in the same manner as described above for the pre-emergent test. This formulation was uniformly sprayed on 2 similar pots containing plants 2 to 3 inches tall (except wild oats, soybean and watergrass which were 3 to 4 inches tall) (approximately 15 to 25 plants per pot) at a dose of 27.5 micrograms/cm$^2$ or in some cases at lower dosages as footnoted in Table 2. After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity, 100 representing complete kill. The results of these tests are summarized in Table 2.

TABLE 1
Pre-Emergence Herbicidal Activity
Application Rate: 27.5 micrograms/cm$^2$, unless otherwise noted

| Compound No. | Broad-Leaf Plants % Phytotoxicity | | | | Grasses % Phytotoxicity | | | |
|---|---|---|---|---|---|---|---|---|
| | Lambs-quarter | Mustard | Pigweed | Soybean | Crabgrass | Watergrass | Wild Oats | Rice |
| 1 | 100 | 100 | 90 | 50 | 100 | 100 | 0 | 0 |
| 2 | 100 | 100 | 50 | 0 | 100 | 100 | 60 | 40 |
| 3 | 100 | 80 | 50 | 0 | 97 | 65 | 30 | 35 |
| 4 | 100 | 100 | 25 | 0 | 88 | 85 | 0 | 0 |
| 5 | 60 | 50 | 50 | 0 | — | 0 | 0 | 0 |
| 6 | 100 | 100 | 95 | 3 | 100 | 100 | 80 | 65 |
| 7[b] | 100 | 100 | 100 | 47 | 100 | 100 | 100 | 100 |
| 8 | 100 | 100 | 100 | 93 | 100 | 100 | 100 | 100 |
| 9[b] | 100 | 100 | 100 | 3 | 100 | 100 | 85 | 99 |
| 10 | 100 | 100 | 100 | 98 | 100 | 100 | 100 | 100 |
| 11 | 100 | 100 | 100 | 80 | 100 | 100 | 100 | 95 |

TABLE 1-continued

Pre-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambs-quarter | Mustard | Pigweed | Soybean | Crabgrass | Watergrass | Wild Oats | Rice |
| 12 | 100 | 100 | 100 | 95 | 100 | 100 | 100 | 100 |
| 13 | 100 | 100 | 100 | 100 | 100 | 100 | 100 | 100 |
| 14 | 100 | 100 | 100 | 75 | 100 | 100 | 100 | 100 |
| 15 | 100 | 100 | 100 | 35 | 100 | 100 | 100 | 98 |
| 16 | 100 | 100 | 75 | 95 | 100 | 100 | 100 | 100 |
| 17 | 100 | 100 | 50 | 30 | 100 | 100 | 100 | 100 |
| 18 | 100 | 100 | 90 | 5 | 100 | 100 | 100 | 100 |
| 19 | 100 | 100 | 100 | 45 | 100 | 100 | 85 | 50 |
| 20 | 100 | 100 | 100 | 40 | 100 | 100 | 92 | 60 |
| 21 | 100 | 100 | 100 | 40 | 100 | 100 | 95 | 65 |
| 22 | 25 | 25 | 60 | 0 | 98 | 40 | 50 | 20 |
| 23 | 93 | 95 | 80 | 30 | 99 | 90 | 75 | 65 |
| 24 | 97 | 85 | 55 | 0 | 100 | 50 | 35 | 25 |
| 25 | 100 | 100 | 100 | 93 | 100 | 100 | 100 | 100 |
| 26 | 100 | 100 | 100 | 98 | 100 | 100 | 100 | 100 |
| 27 | 98 | 100 | 99 | 30 | 100 | 100 | 100 | 88 |
| 28 | 100 | 100 | 100 | 13 | 100 | 100 | 90 | 25 |
| 29 | 98 | 98 | 100 | 80 | 100 | 88 | 55 | 45 |
| 30 | 98 | 90 | 95 | 30 | 60 | 40 | 55 | 40 |
| 31 | 100 | 100 | 100 | 20 | 98 | 98 | 98 | 70 |
| 32 | 100 | 100 | 100 | 35 | 100 | 100 | 85 | 70 |
| 33 | 75 | 40 | 35 | 0 | 60 | 55 | 65 | 50 |
| 34 | 100 | 100 | 100 | 100 | 100 | 100 | 100 | 95 |
| 35 | 100 | 100 | 100 | 85 | 100 | 100 | 98 | 85 |
| 36 | 99 | 100 | 100 | 30 | 100 | 93 | 90 | 35 |
| 37 | 80 | 85 | 55 | 55 | 83 | 63 | 20 | 0 |
| 38 | 100 | 100 | 100 | 100 | 100 | 100 | 100 | 100 |
| 39[a] | 98 | 100 | 100 | 85 | 100 | 100 | 100 | 85 |
| 40 | 100 | 100 | 100 | 90 | 100 | 100 | 100 | 72 |
| 41[a] | 100 | 85 | 98 | 40 | 100 | 85 | 80 | 55 |
| 42 | 100 | 100 | 100 | 93 | 100 | 100 | 98 | 98 |
| 43 | 95 | 100 | 100 | 65 | 100 | 100 | 75 | 65 |
| 44 | 0 | 0 | 0 | 0 | 0 | 0 | 0 | 0 |
| 45 | 90 | 100 | 100 | 50 | 100 | 90 | 80 | 50 |
| 46 | 100 | 100 | 100 | 100 | 100 | 100 | 100 | 100 |
| 47 | 100 | 100 | 100 | 70 | 100 | 100 | 100 | 80 |
| 48 | 15 | 50 | 30 | 30 | 0 | 30 | 0 | 0 |
| 49 | 65 | 50 | 0 | 18 | 0 | 0 | 0 | 0 |
| 50 | 35 | 10 | 0 | 0 | 60 | 20 | 0 | 0 |
| 51 | 98 | 100 | 100 | 60 | 98 | 80 | 85 | 25 |
| 52 | 100 | 100 | 100 | 100 | 100 | 100 | 100 | 100 |
| 53 | 100 | 100 | 85 | 0 | 35 | 20 | 15 | 0 |
| C-1 | 0 | 0 | 0 | 0 | 0 | 0 | 0 | 0 |
| C-2 | 0 | 0 | 0 | 0 | 0 | 0 | 0 | 0 |
| C-3 | 0 | 0 | 0 | 0 | 0 | 0 | 0 | 0 |
| C-4 | 0 | 0 | 0 | 0 | 0 | 0 | 0 | 0 |
| C-5 | 0 | 0 | 0 | 0 | 0 | 0 | 0 | 0 |
| C-6 | 0 | 0 | 0 | 0 | 0 | 0 | 0 | 0 |
| C-7 | 0 | 0 | 0 | 0 | 0 | 0 | 0 | 0 |
| C-8 | 0 | 0 | 0 | 0 | 0 | 0 | 0 | 0 |
| C-9 | 0 | 0 | 0 | 0 | 0 | 0 | 0 | 0 |
| C-10 | 0 | 0 | 0 | 0 | 0 | 0 | 0 | 0 |
| C-11 | 0 | 0 | 0 | 0 | 0 | 0 | 0 | 0 |
| C-12 | 0 | 0 | 0 | 0 | 0 | 0 | 0 | 0 |
| C-13 | 0 | 0 | 0 | 0 | 0 | 0 | 0 | 0 |
| C-14[a] | 0 | 0 | 0 | 0 | 0 | 0 | 0 | 0 |
| C-15 | 0 | 0 | 0 | 0 | 0 | 0 | 0 | 0 |
| C-16 | 0 | 0 | 0 | 0 | 0 | 0 | 0 | 0 |

[a]tested at 15.6 micrograms/cm²
[b]tested at 4.4 micrograms/cm²

TABLE 2

Post-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambs-quarter | Mustard | Pigweed | Soybean | Crabgrass | Watergrass | Wild Oats | Rice |
| 1 | 0 | 60 | 0 | 0 | 0 | 0 | 0 | 0 |
| 2 | 20 | 45 | 40 | 30 | 0 | 0 | 0 | 0 |
| 3 | 0 | 0 | 0 | 0 | 0 | 0 | 0 | 0 |
| 4 | 0 | 30 | 0 | 0 | 0 | 0 | 0 | 0 |
| 5 | 0 | 25 | 20 | 30 | 0 | 0 | 0 | 0 |
| 6 | 45 | 90 | 35 | 35 | 0 | 0 | 0 | 0 |
| 7[b] | 37 | 58 | 60 | 67 | 13 | 50 | 50 | 7 |
| 8 | 85 | 100 | 90 | 75 | 100 | 95 | 100 | 93 |
| 9[b] | 70 | 88 | 73 | 33 | 23 | 50 | 42 | 17 |
| 10 | 93 | 100 | 90 | 93 | 70 | 80 | 65 | 45 |
| 11 | 55 | 75 | 65 | 60 | 40 | 60 | 25 | 20 |
| 12 | 80 | 100 | 95 | 70 | 80 | 70 | 70 | 40 |
| 13 | 80 | 90 | 50 | 75 | 55 | 65 | 65 | 15 |
| 14 | 65 | 85 | 65 | 55 | 45 | 65 | 60 | 20 |
| 15 | 80 | 93 | 80 | 65 | 50 | 75 | 60 | 20 |
| 16 | 65 | 65 | 70 | 70 | 20 | 20 | 20 | 0 |
| 17 | — | — | — | — | — | — | — | — |
| 18 | 90 | 100 | 93 | 60 | 30 | 25 | 35 | 0 |
| 19 | 60 | 65 | 70 | 70 | 0 | 0 | 0 | 0 |
| 20 | 70 | 85 | 50 | 65 | 40 | 50 | 25 | 20 |
| 21 | 93 | 95 | — | 75 | 25 | 20 | 25 | 0 |
| 22 | 30 | 25 | 25 | 20 | 25 | 0 | 0 | 0 |
| 23 | 35 | 43 | 0 | 35 | 0 | 0 | 0 | 0 |
| 24 | 0 | 10 | 20 | 10 | 0 | 0 | 0 | 0 |
| 25 | 65 | 100 | 88 | 70 | 75 | 75 | 30 | 30 |
| 26 | 90 | 95 | 80 | 80 | 55 | 80 | 70 | 25 |
| 27 | 55 | 80 | 50 | 55 | 20 | 25 | 25 | 0 |
| 28 | 60 | 50 | 55 | 55 | 30 | 20 | 0 | 0 |
| 29 | 50 | 85 | 15 | 40 | 0 | 0 | 0 | 0 |
| 30 | 23 | 45 | 25 | 10 | 0 | 0 | 0 | 0 |
| 31 | 25 | 65 | 45 | 25 | 0 | 0 | 0 | 0 |
| 32 | 40 | 40 | 35 | 20 | 20 | 20 | 20 | 0 |
| 33 | 25 | 40 | 40 | 35 | 0 | 0 | 0 | 0 |
| 34 | 45 | 80 | 45 | 35 | 20 | 35 | 35 | 0 |
| 35 | 65 | 60 | 55 | 35 | 55 | 55 | 50 | 40 |
| 36 | 45 | 50 | 45 | 45 | 0 | 0 | 0 | 0 |
| 37 | 20 | 15 | 0 | 40 | 0 | 0 | 0 | 0 |
| 38 | 83 | 100 | 90 | 78 | 62 | 80 | 70 | 35 |
| 39[a] | 85 | 95 | 70 | 75 | 45 | 40 | 35 | 35 |
| 40 | 78 | 95 | 72 | 40 | 40 | 45 | 30 | 28 |
| 41[a] | 75 | 75 | 75 | 65 | 0 | 0 | 0 | 0 |
| 42 | 90 | 100 | 75 | 60 | 50 | 75 | 40 | 20 |
| 43 | 75 | 100 | 80 | 40 | 55 | 85 | 55 | 15 |
| 44 | 0 | 60 | 30 | 0 | 0 | 0 | 0 | 0 |
| 45 | 20 | 30 | 30 | 30 | 30 | 40 | 50 | 0 |
| 46 | 50 | 100 | 0 | 95 | 70 | 70 | 75 | 30 |
| 47 | 90 | 90 | — | 80 | 30 | 20 | 20 | 0 |
| 48 | 0 | 0 | 0 | 0 | 0 | 0 | 0 | 0 |
| 49 | 0 | 0 | 0 | 0 | 0 | 0 | 0 | 0 |
| 50 | 0 | 0 | 0 | 0 | 0 | 0 | 0 | 0 |
| 51 | 30 | 80 | — | 55 | 0 | 0 | 0 | 0 |
| 52 | 70 | 80 | 75 | 55 | 0 | 35 | 30 | 0 |
| 53 | 20 | 20 | 0 | 0 | 0 | 0 | 0 | 0 |
| C-1 | 0 | 0 | 0 | 0 | 0 | 0 | 0 | 0 |
| C-2 | 0 | 0 | 15 | 0 | 0 | 0 | 0 | 0 |
| C-3 | 0 | 0 | 0 | 0 | 0 | 0 | 0 | 0 |
| C-4 | 0 | 0 | 0 | 0 | 0 | 0 | 0 | 0 |
| C-5 | 0 | 0 | 0 | 0 | 0 | 0 | 0 | 0 |
| C-6 | 0 | 0 | 0 | 0 | 0 | 0 | 0 | 0 |
| C-7 | 0 | 0 | 0 | 0 | 0 | 0 | 0 | 0 |
| C-8 | 0 | 0 | 0 | 0 | 0 | 0 | 0 | 0 |
| C-9 | 0 | 0 | 0 | 0 | 0 | 0 | 0 | 0 |
| C-10 | 0 | 0 | 0 | 0 | 0 | 0 | 0 | 0 |
| C-11 | 0 | 0 | 0 | 0 | 0 | 0 | 0 | 0 |
| C-12 | 15 | 30 | 0 | 0 | 0 | 0 | 0 | 0 |
| C-13 | 0 | 0 | 0 | 0 | 0 | 0 | 0 | 0 |
| C-14[a] | 0 | 0 | 0 | 0 | 0 | 0 | 0 | 0 |
| C-15 | 0 | 10 | 0 | 0 | 0 | 0 | 0 | 0 |
| C-16 | 0 | 0 | 0 | 0 | 0 | 0 | 0 | 0 |

[a]tested at 15.6 micrograms/cm²
[b]tested at 4.4 micrograms/cm²

As can be seen from the above Table 1, the compounds of the invention generally exhibit a broad spectrum of excellent pre-emergence phytotoxic activity and especially so Compounds Nos. 7–9, 13–18, 38, 39 and 46. Also certain of these compounds exhibited reduced phytotoxicity with respect to soybean while retaining excellent pre-emergent phytotoxicity with respect to both broadleaf and grassy weeds. As shown by Table 2 a number of the compounds also exhibited from modest to very good post-emergence phytotoxicity but are primarily pre-emergence herbicides. In contrast to this it can be seen that none of the comparison compounds exhibited any pre-emergence herbicidal activity whatsoever and only three of the comparison compounds (and none of the reference compounds) exhibited any post-emergence activity and this was at a very low level. Also, as can be seen from Table 1 the compounds of the invention having a 4-(3-trifluoromethylphenyl) substitutent and/or a 5-methylamino exhibited substantially superior phytotoxicity.

Obviously, many modifications and variations of the invention described hereinabove and below can be made without departing from the essence and scope thereof.

What is claimed is:

1. A compound- having the formula:

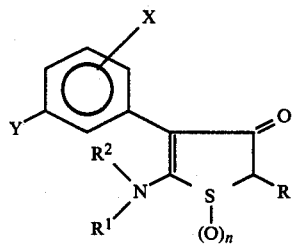
(I)

wherein n is 0, 1 or 2; R is lower alkyl, cycloalkyl having 3 through 7 carbon atoms; (cycloalkyl)alkylene having 3 through 7 carbon atoms in the cycloalkyl moiety and 1 through 3 carbon atoms in the alkylene moiety; lower alkenyl; haloalkyl having 1 through 4 carbon atoms and 1 through 3 halo atoms independently selected from the group of fluoro, chloro, bromo or iodo; haloalkenyl having 2 through 4 carbon atoms and 1 through 3 halo atoms independently selected from the group of fluoro, chloro, bromo, or iodo; lower alkoxy; lower alkylthio; lower alkoxyalkyl wherein the alkyl and alkoxy moieties independently have 1 through 3 carbon atoms; alkylthioalkyl wherein the alkyl moieties independently have 1 through 3 carbon atoms; phenyl, naphth-1-yl, inden-1-yl; 4-fluorophenyl; arylalkylene having 1 through 3 carbon atoms in the alkylene moiety and wherein the aryl moiety is phenyl, naphth-1-yl or inden-1-yl; or R is a substituted aryl or substituted arylalkylene selected from the group having the formulas:

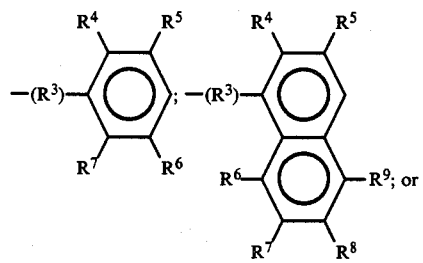

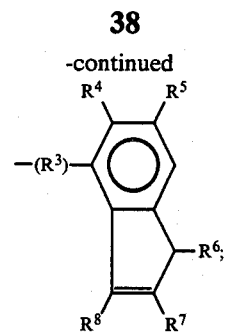

wherein one, two or three of $R^4$, $R^5$, $R^6$, $R^7$, $R^8$, and $R^9$ are independently selected from the group of lower alkyl, lower alkoxy, halo, nitro, or haloalkyl having 1 through 3 carbon atoms and 1 through 3 of the same or different halo atoms, and the remainder of $R^4$, $R^5$, $R^6$, $R^7$, $R^8$ and $R^9$ are hydrogen; and $R^3$ is a single bond or alkylene having 1 through 3 carbon atoms;

$R^1$ is hydrogen or alkyl having 1 through 4 carbon atoms;

$R^2$ is hydrogen, alkyl having 1 through 4 carbon atoms, alkenyl having 3 or 4 carbon atoms, lower alkoxycarbonylalkyl having from 1 through 4 carbon atoms in the alkoxy moiety and from 1 through 4 carbon atoms in the alkyl moiety; lower alkoxyalkyl wherein the alkoxy and alkyl moieties independently have 1 through 3 carbon atoms, or lower alkylthioalkyl wherein the alkyl moieties independently have 1 through 3 carbon atoms; or $R^1$ and $R^2$ together with the nitrogen atom to which they are joined form a saturated or unsaturated nitrogen heterocycle having 3 through 6 carbon atoms one of which is nitrogen and the remainder are carbon atoms;

X is hydrogen, lower alkyl, lower alkoxy, halo, or trifluoromethyl and can be at any available position on the phenyl ring; and Y is lower alkyl, lower alkoxy, halo, lower haloalkyl having 1 through 4 carbon atoms and 1 through 3 of the same or different halo atoms, lower haloalkoxy having 1 through 4 carbon atoms and 1 through 3 of the same or different halo atoms, or lower haloalkylthio having 1 through 4 carbon atoms and 1 through 3 of the same or different halo atoms, with the proviso that when Y is halo then R, $R^1$ and $R^2$ are not all hydrogen and the further proviso that when Y is other than trifluoromethyl and X is other than hydrogen, and $R^1$ and $R^2$ are each hydrogen then R is methyl, ethyl, propyl, 2-halophenyl, 2-lower alkylphenyl or 4-fluorophenyl;

and compatible salts thereof.

2. A compound having the formula:

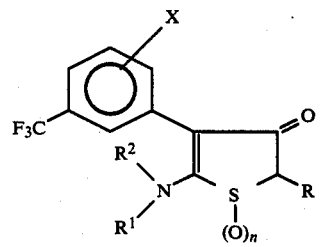
(I)

wherein n is 0, 1, or 2; R is lower alkyl, cycloalkyl having 3 through 7 carbon atoms; (cycloalkyl)alkyl having 3 through 7 carbon atoms in the cycloalkyl moiety and 1 through 3 carbon atoms in the alkylene moiety; lower alkenyl; haloalkyl having 1 through 4 carbon atoms and 1 through 3 halo atoms independently selected from the group of fluoro, chloro, bromo or iodo; haloalkenyl having 2 through 4 carbon atoms and 1 through 3 halo atoms independently selected from the group of fluoro, chloro, bromo, or iodo; lower alkoxy; lower alkylthio; lower alkoxyalkyl wherein the alkyl and alkoxy moieties independently have 1 through 3 carbon atoms; lower alkylthioalkyl wherein the alkyl moieties independently have 1 through 3 carbon atoms; phenyl, naphth-1-yl, inden-1-yl; 4-fluorophenyl; arylalkylene having 1 through 3 carbon atoms in the alkylene moiety and wherein the aryl moiety is phenyl, naphth-1-yl or inden-1-yl; or R is a substituted aryl or substituted arylalkylene selected from the group having the formulas:

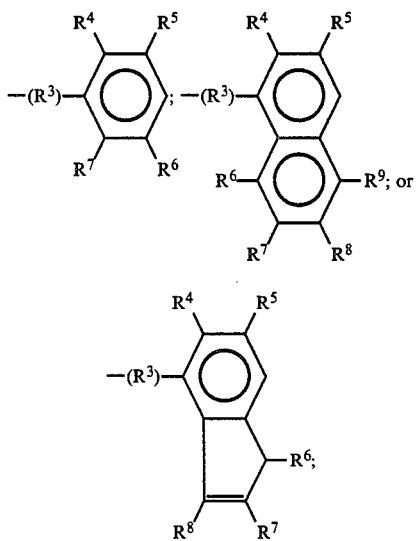

wherein one, two or three of $R^4$, $R^5$, $R^6$, $R^7$, $R^8$, and $R^9$ are independently selected from the group of lower alkyl, lower alkoxy, halo, nitro, or haloalkyl having 1 through 3 carbon atoms and 1 through 3 of the same or different halo atoms, and the remainder are hydrogen; and $R^3$ is a single bond or alkylene having 1 through 3 carbon atoms;

$R^1$ is hydrogen or alkyl having 1 through 4 carbon atoms:

$R^2$ is hydrogen, alkyl having 1 through 4 carbon atoms, alkenyl having 3 or 4 carbon atoms, lower alkoxycarbonylalkyl, lower alkoxyalkyl or lower alkylthioalkyl; or $R^1$ and $R^2$ together with the nitrogen atom to which they are joined form a saturated or unsaturated nitrogen heterocycle having 3 through 6 carbon atoms one of which is nitrogen and the remainder are carbon atoms;

X is hydrogen, lower alkyl, lower alkoxy, halo, or trifluoromethyl and can be at any available position on the phenyl ring;

and compatible salts thereof.

3. The compound of claim 2 wherein $R^1$ and $R^2$ are independently selected from the group of hydrogen, methyl, ethyl or propyl.

4. The compound of claim 3 wherein R is methyl, ethyl or n-propyl.

5. The compound of claim 4 wherein one of $R^1$ or $R^2$ is hydrogen or methyl and the other is hydrogen, methyl or ethyl.

6. The compound of claim 2 wherein X is hydrogen.

7. The compound of claim 3 wherein X is hydrogen.

8. The compound of claim 4 wherein X is hydrogen.

9. The compound of claim 2 wherein R is methyl, ethyl, n-propyl, butyl, phenyl or a monosubstituted aryl.

10. The compound of claim 9 wherein R is phenyl or monosubstituted phenyl.

11. The compound of claim 10 wherein R is phenyl, monohalophenyl, or mono lower alkylphenyl.

12. The compound of claim 10 wherein X is hydrogen.

13. The compound of claim 1 wherein said compound is selected from the group having the formula:

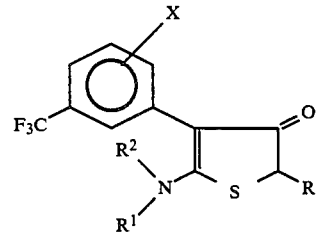

wherein R, $R^1$, $R^2$ and X are as defined in claim 1; and compatible cation salts thereof.

14. The compound of claim 13 wherein $R^1$ and $R^2$ are independently hydrogen or methyl or ethyl.

15. The compound of claim 13 wherein R is methyl, ethyl, propyl or n-butyl.

16. The compound of claim 13 wherein X is hydrogen.

17. The compound of claim 16 wherein $R^1$ and $R^2$ are independently hydrogen, methyl, or ethyl.

18. The compound of claim 17 wherein $R^1$ is methyl, ethyl, or propyl.

19. The compound of claim 18 wherein R is methyl and one of $R^1$ or $R^2$ is hydrogen and the other is methyl.

20. The compound of claim 18 wherein R is ethyl and one of $R^1$ or $R^2$ is hydrogen and the other is methyl.

21. The compound of claim 18 wherein R is n-propyl and one of $R^1$ and $R^2$ is hydrogen and the other is methyl.

22. The compound of claim 16 wherein R is methyl, ethyl or n-propyl and one of $R^1$ or $R^2$ is hydrogen and the other is methyl.

23. The compound of claim 14 wherein R is phenyl, 2-halophenyl, 4-fluorophenyl, or 2-lower alkylphenyl.

24. The compound of claim 14 wherein R is phenyl, 2-fluorophenyl, 4-fluorophenyl, 2-methylphenyl.

25. The compound of claim 23 wherein $R^1$ and $R^2$ are independently hydrogen or methyl and X is hydrogen.

26. The compound of claim 25 wherein R is 4-fluorophenyl.

27. The compound of claim 25 wherein R is phenyl.

28. The compound of claim 25 wherein R is 2-methylphenyl.

29. The compound of claim 25 wherein R is phenyl, 2-methylphenyl, 2-fluorophenyl, 2-chlorophenyl or 4-fluorophenyl.

30. A herbicidal composition comprising a herbicidally effective amount of a compound according to claim 1, or mixtures of such compounds, and a compatible carrier.

31. A herbicidal composition comprising a herbicidally effective amount of a compound according to claim 22, or mixtures thereof, and a compatible carrier.

32. A method for controlling plants which comprises applying a herbicidally effective amount of a compound according to claim 1, or mixtures thereof, to the foliage or growth medium or potential growth medium of said plants.

33. A method for controlling plants which comprises applying a herbicidally effective amount of a compound according to claim 22, or mixtures thereof, to the foliage or growth medium or potential growth medium of said plants.

34. A plant growth regulating composition which comprises an amount of a compound according to claim 1, or mixtures thereof, effective to alter the growth pattern of plants.

35. A method for regulating the growth of plants which comprises applying to the foliage of said plants or their growth medium an amount of a compound according to claim 1, or mixtures thereof, effective to alter the growth pattern of such plants.

36. The compound of claim 1 wherein R is methyl, ethyl, propyl, phenyl or monosubstituted phenyl.

37. The compound of claim 1 wherein $R^1$ and $R^2$ are independently selected from the group of hydrogen, methyl, ethyl or propyl.

38. The compound of claim 1 wherein one of $R^1$ or $R^2$ is hydrogen and the other is methyl or ethyl.

39. The compound of claim 38 wherein R is methyl, ethyl phenyl 2-halophenyl, or 2-lower alkylphenyl.

* * * * *